US011160491B2

(12) United States Patent
Aung et al.

(10) Patent No.: US 11,160,491 B2
(45) Date of Patent: Nov. 2, 2021

(54) DEVICES, SYSTEMS, AND METHODS FOR MONITORING WOUNDS

(71) Applicant: Hill-Rom Services, Inc., Batesville, IN (US)

(72) Inventors: Aye Aung, Singapore (SG); Xue Wang, Singapore (SG); Qinglin Mok, Singapore (SG); Aye Min Htun, Singapore (SG); Yaolong Lou, Singapore (SG)

(73) Assignee: Hill-Rom Services, Inc., Batesville, IN (US)

( * ) Notice: Subject to any disclaimer, the term of this patent is extended or adjusted under 35 U.S.C. 154(b) by 270 days.

(21) Appl. No.: 16/120,937

(22) Filed: Sep. 4, 2018

(65) Prior Publication Data

US 2019/0083025 A1 Mar. 21, 2019

Related U.S. Application Data

(60) Provisional application No. 62/557,483, filed on Sep. 12, 2017.

(51) Int. Cl.
*A61B 5/00* (2006.01)
*G16H 50/30* (2018.01)
(Continued)

(52) U.S. Cl.
CPC ............ *A61B 5/445* (2013.01); *A61B 5/0077* (2013.01); *A61B 5/1032* (2013.01);
(Continued)

(58) Field of Classification Search
CPC ..... A61B 5/445; A61B 5/0077; A61B 5/1032; A61B 5/1075; A61B 5/1079;
(Continued)

(56) References Cited

U.S. PATENT DOCUMENTS 8,606,345 B2 * 12/2013 Taylor ................. A61B 5/0059
600/407
2002/0062114 A1 * 5/2002 Murai ..................... G01N 5/02
604/385.01

(Continued)

FOREIGN PATENT DOCUMENTS

EP 2662029 A2 * 11/2013 ............. A61B 5/445

OTHER PUBLICATIONS

Iizaka, S., et al. "Quantitative estimation of exudate volume for full-thickness pressure ulcers: the ESTimation method." Journal of wound care 20.10 (2011): 453-463. (Year: 2011).*

(Continued)

*Primary Examiner* — Sean D Mattson
(74) *Attorney, Agent, or Firm* — Dinsmore & Shohl LLP

(57) ABSTRACT

Devices, systems, and methods for monitoring and determining characteristics of wounds on a subject are disclosed. A monitoring device includes an imaging component and a computing device communicatively coupled to the imaging component. The imaging component includes a light emitting component that emits light at a calibrated wavelength, a laser emitting device, and an imaging device. The computing device directs the light emitting component to emit the light at the calibrated wavelength, directs the imaging component to cause the laser emitting device to emit a laser projection toward the wound, receives, from the imaging component, image data captured by the imaging device, determines, from the image data, the characteristics of the wound, and scores the wound based on the characteristics of the wound to obtain a wound score. The characteristics include one or more of a size of the wound, a type of tissue, and an amount of exudate.

18 Claims, 13 Drawing Sheets

(51) Int. Cl.
*G16H 30/40* (2018.01)
*G16H 50/20* (2018.01)
*G06T 7/62* (2017.01)
*A61B 5/103* (2006.01)
*A61B 5/107* (2006.01)
*G06T 7/00* (2017.01)
*H04N 5/235* (2006.01)

(52) U.S. Cl.
CPC .......... *A61B 5/1075* (2013.01); *A61B 5/1079* (2013.01); *A61B 5/7264* (2013.01); *A61B 5/7475* (2013.01); *G06T 7/0012* (2013.01); *G06T 7/62* (2017.01); *G16H 30/40* (2018.01); *G16H 50/20* (2018.01); *G16H 50/30* (2018.01); *H04N 5/2353* (2013.01); *A61B 2576/02* (2013.01); *G06T 2200/24* (2013.01); *G06T 2207/10024* (2013.01); *G06T 2207/10144* (2013.01); *G06T 2207/30088* (2013.01)

(58) Field of Classification Search
CPC . A61B 5/7264; A61B 5/7475; A61B 2576/02; G16H 50/30; G16H 50/40; G16H 50/20; G06T 7/62; G06T 7/0012; G06T 2200/24; G06T 2207/10024; G06T 2207/10144; G06T 2207/30088; H04N 5/2353
See application file for complete search history.

(56) References Cited

U.S. PATENT DOCUMENTS

| | | | |
|---|---|---|---|
| 2007/0002165 A1* | 1/2007 | Parks | H04N 5/2353 348/367 |
| 2009/0213213 A1* | 8/2009 | Fright | A61B 5/7275 348/77 |
| 2010/0091104 A1* | 4/2010 | Sprigle | A61B 5/445 348/136 |
| 2013/0137991 A1 | 5/2013 | Fright et al. | |
| 2015/0119721 A1* | 4/2015 | Pedersen | G06T 7/0012 600/476 |
| 2016/0100790 A1 | 4/2016 | Cantu et al. | |
| 2016/0284084 A1* | 9/2016 | Gurcan | G06T 7/0016 |
| 2017/0079575 A1* | 3/2017 | Darling | A61B 5/742 |
| 2017/0236281 A1 | 8/2017 | Dacosta | |
| 2018/0114318 A1* | 4/2018 | Grupp | A61B 5/02042 |

OTHER PUBLICATIONS

Wannous, Hazem, Sylvie Treuillet, and Yves Lucas. "Robust tissue classification for reproducible wound assessment in telemedicine environments." Journal of Electronic Imaging 19.2 (2010): 023002. (Year: 2010).*
National Pressure Ulcer Advisory Panel "PUSH Tool 3.0 (web version)". http://www.npuap.org/resources/educational-and-clinical-resources/push-tool/push-tool/.
Journal of Wound, Ostomy and Continence Nursing. May 2010. "Bates-Jensen Wound Assessment Tool: Pictorial Guide Validation Project". https://www.ncbi.nlm.nih.gov/pubmed/20386331.
Aung Aye, Boon Poh NG, and Susanto Rahardja. "A robust watermarking scheme using sequency-ordered complex Hadamard transform." Journal of Signal Processing Systems 64.3 (2011): 319-333.
Chou R., Dana T., Bougatsos C., Blazina I., Starmer A., Reitel K., Buckley D. Pressure Ulcer Risk Assessment and Prevention: Comparative Effectiveness. Comparative Effectiveness Review No. 87. AHRQ Publication No. 12(13)—EHC148-EF. Rockville, MD: Agency for Healthcare Research and Quality. May 2013. www.effectivehealthcare.ahrq.gov/reports/final.cfm.
C. Allison Russo, M.P.H., Claudia Steiner, M.D., M.P.H., and William Spector, Ph.D. "Hospitalizations Related to Pressure Ulcers among Adults 18 Years and Older, 2006". Agency for Healthcare Research and Quality, Healthcare Cost and Utilization Project, Statistical Brief #64 (2008). https://www.hcup-us.ahrq.gov/reports/statbriefs/sb64.pdf.
Agency for Healthcare Research and Quality. "Preventing Pressure Ulcers in Hospitals". https://www.ahrq.gov/professionals/systems/hospital/pressureulcertoolkit/putool1.html.
Naitonal Pressure Ulcer Advisory Panel. "Pressure Ulcer Healing Chart". http://www.npuap.org/wp-content/uploads/2012/03/push3.pdf.
Communication Pursuant to Article 94(3) EPC pertaining to European Patent Application No. 18193546.1, dated Apr. 6, 2021, 10 pages.

* cited by examiner

| | 0 | 1 | 2 | 3 | 4 | 5 | SUB - SCORE |
|---|---|---|---|---|---|---|---|
| LENGTH X WIDTH | 0 | < 0.3 | 0.3 - 0.6 | 0.7 - 1.0 | 1.1 - 2.0 | 2.1 - 3.0 | |
| (in cm²) | | 6 | 7 | 8 | 9 | 10 | |
| | | 3.1 - 4.0 | 4.1 - 8.0 | 8.1 - 12.0 | 12.1 - 24.0 | > 24.0 | |
| EXUDATE AMOUNT | 0 NONE | 1 LIGHT | 2 MODERATE | 3 HEAVY | | | SUB - SCORE |
| TISSUE TYPE | 0 CLOSED | 1 EPITHELIAL TISSUE | 2 GRANULATION TISSUE | 3 SLOUGH | 4 NECROTIC TISSUE | | SUB - SCORE |
| | | | | | | | TOTAL SCORE |

1105 → (LENGTH X WIDTH rows)
1110 → (EXUDATE AMOUNT row)
1115 → (TISSUE TYPE row)

FIG. 11

DEVICES, SYSTEMS, AND METHODS FOR MONITORING WOUNDS

CROSS-REFERENCE TO RELATED APPLICATION

The present application claims priority to U.S. Provisional Patent Application No. 62/557,483, filed Sep. 12, 2017 and entitled "Devices, Systems, and Methods for Monitoring Wounds," the contents of which is incorporated herein in its entirety.

BACKGROUND

Field

The present specification generally relates to wound monitoring systems and methods and, more specifically, to devices for monitoring pressure wounds that are portable and can be used by non-medical personnel, as well as systems and methods for using such devices.

Technical Background

It may be necessary to monitor particular areas of a subject's body to avoid recurrent health issues. For example, a bedridden subject may be susceptible to development of wounds, such as pressure wounds or the like. Pressure wounds may be monitored by medical personnel such that they are adequately treated before becoming detrimental to the subject's health. However, it may be inconvenient and/or expensive for the subject to travel to the medical personnel, for the medical personnel to travel to the subject, or to hospitalize the subject to ensure that the subject is adequately monitored. In addition, subjects, family members of subjects, friends of subjects, and/or the like may not be adequately trained to identify the existence and severity of a wound and/or communicate the correct information to medical personnel. Furthermore, existing devices that are used to monitor pressure wounds or the like are generally not portable and/or require specific training and knowledge to operate, and thus are not operable by laypersons.

Accordingly, a need exists for devices, systems, and methods that provide non-medical personnel with an ability to image portions of a subject's body, particularly areas containing pressure wounds on the subject's body, determine characteristics of the wounds, score the wounds, and convey the necessary information to medical personnel such that the pressure wounds can be effectively monitored and timely treated.

SUMMARY

In one embodiment, a monitoring device for determining characteristics of a wound on a subject includes an imaging component and a computing device communicatively coupled to the imaging component. The imaging component includes a light emitting component that emits light at a calibrated wavelength, a laser emitting device, and an imaging device. The computing device directs the light emitting component to emit the light at the calibrated wavelength, directs the imaging component to cause the laser emitting device to emit a laser projection toward the wound, receives, from the imaging component, image data captured by the imaging device, determines, from the image data, the characteristics of the wound, and scores the wound based on the characteristics of the wound to obtain a wound score. The characteristics include one or more of a size of the wound, a type of tissue, and an amount of exudate.

In another embodiment, a method of obtaining characteristics regarding a wound on a subject includes directing a user to position an imaging component of a wound monitoring device such that the imaging component faces the wound without contacting the wound, directing a light emitting component to emit light at a calibrated wavelength, directing the imaging component to cause a laser emitting device to emit a laser projection toward the wound, receiving, from the imaging component, image data captured by an imaging device, determining the characteristics from the image data, and scoring the wound based on the characteristics to obtain a wound score. The characteristics include one or more of a size of the wound, a type of tissue, and an amount of exudate.

In yet another embodiment, a monitoring device for determining characteristics of a wound on a subject includes an imaging component and a computing device communicatively coupled to the imaging component. The imaging component includes a light emitting component that emits light at a calibrated wavelength, a laser emitting device, and an imaging device. The computing device includes a processing device and a non-transitory, processor-readable storage medium, the non-transitory, processor-readable storage medium having one or more processor readable and executable instructions that, when executed, cause the processing device to direct the light emitting component to emit the light at the calibrated wavelength, direct the imaging component to cause the laser emitting device to emit a laser projection toward the wound, receive, from the imaging component, image data captured by the imaging device, determine, from the image data, the characteristics of the wound, and score the wound based on the characteristics of the wound to obtain a wound score. The characteristics include one or more of a size of the wound, a type of tissue, and an amount of exudate.

In yet another embodiment, a system for determining characteristics of a wound on a subject includes a monitoring device and an external computing device communicatively coupled to the monitoring device. The monitoring device includes an imaging component having a light emitting component, a laser emitting device, and an imaging device. The monitoring device directs placement of the monitoring device at a location adjacent to the wound without contacting the wound, emits, via the light emitting component, light at a calibrated wavelength, emits, via the laser emitting device, a laser projection toward the wound, captures, via the imaging device, image data corresponding to the wound, determines, from the image data, the characteristics of the wound, and assigns a score to the wound based on the characteristics of the wound. The characteristics include one or more of a size of the wound, a type of tissue, and an amount of exudate. The external computing device receives the score and provides the score to one or more users.

In yet another embodiment, a method of obtaining characteristics regarding a wound on a subject includes positioning an imaging component of a wound monitoring device such that the imaging component faces the wound without contacting the wound, emitting light at a calibrated wavelength, emitting a laser projection toward the wound, and collecting image data with an imaging device. The wound monitoring device determines the characteristics from the image data, the characteristics including one or more of a size of the wound, a type of tissue, and an amount of exudate, and scores the wound based on the characteristics to obtain a wound score.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

FIG. 11 depicts a plurality of scoring charts that are used for determining a score for a wound size, an exudate amount, and a tissue type according to one or more embodiments shown or described herein.

DETAILED DESCRIPTION

Figure 1A:
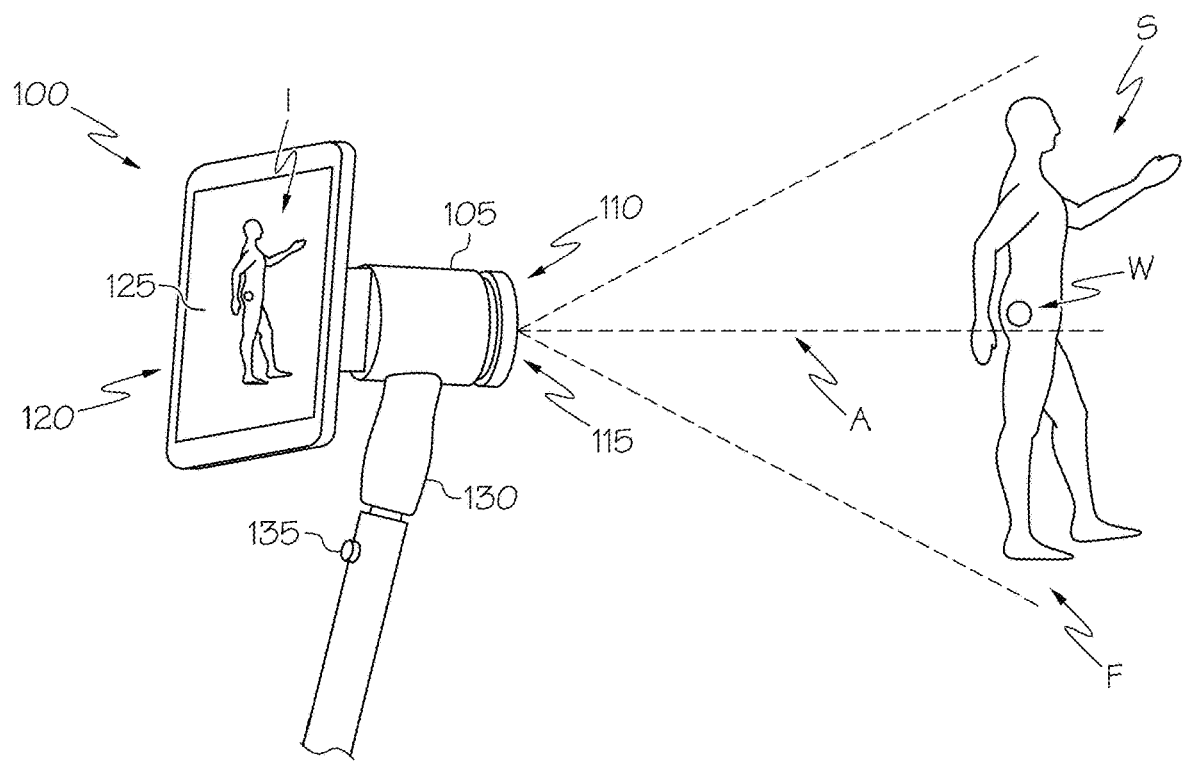
FIG. 1A depicts a side perspective view of an illustrative pressure wound monitoring device that images a wound according to one or more embodiments shown or described herein.

Reference will now be made in detail to embodiments of devices, systems, and methods for determining characteristics of one or more wounds on a subject, examples of which are illustrated in the accompanying drawings. Whenever possible, the same reference numerals will be used throughout the drawings to refer to the same or like parts. One embodiment of a device for determining characteristics of one or more wounds is depicted in FIG. 1A, in which the device includes an imaging component communicatively coupled to a computing device. The imaging component contains devices that are configured to emit light at a calibrated wavelength and emit laser light that is used to determine a distance between the device and a wound, and an imaging device that obtains images of the wound from calibrated wavelength light reflected from the wound. The computing device directs operation of the imaging component, receives image data, determines wound characteristics, scores the wound characteristics, and transmits the score and/or additional data to an external device that is operated by medical personnel. Accordingly, the wound can be remotely tracked by medical personnel to determine whether the wound is healing or worsening without requiring non-medical personnel to determine and convey information regarding the wound. In addition, the score and/or other imaging data can be stored as a baseline and later accessed for purposes of determining how healing is progressing or regressing.

The computing device may generally score the wound using programming that adheres to guidelines that have been promulgated for wound assessment. Illustrative examples of guidelines include, but are not limited to, the Pressure Ulcer for Healing (PUSH) guidelines developed by the National Pressure Ulcer Advisory Panel (NPUAP) and the Bates-Jensen Wound Assessment Tool (BWAT). The PUSH guidelines are based on three characteristics: size of the wound (i.e., length×width), an amount of exudate, and a tissue type. The BWAT guidelines are based on thirteen characteristics: wound size, depth, edges, undermining, necrotic tissue type, necrotic tissue amount, granulation tissue amount, epithelization tissue amount, exudate type, exudate amount, surrounding skin color, edema, and induration. While the present disclosure generally relates to wound size, exudate amount, and tissue type characteristics in automatically assessing the wound, it should be understood that the computing device described herein may further be utilized to detect, measure, and score other characteristics, including the characteristics described above.

As used herein, the term "exudate" refers to a clear, straw colored liquid produced by the body in response to tissue damage. Although exudate is primarily water, it also includes cellular materials, antibodies, and oxygen. In the immediate response to an injury, exudate is produced by the body to flush away any foreign materials from the wound site. While exudate is an important component of wound healing, excess exudate in response to chronic inflammation caused by pressure ulcers or the like can aggravate a wound. Monitoring the amount of exudate by determining the size of the exudate stain on a bandage covering the wound can be used to determine whether a wound is healing or worsening.

The phrase "communicatively coupled" is used herein to describe the interconnectivity of various components of the devices for determining characteristics of a wound on a subject, as well as the systems encompassing such devices and means that the components are connected either through wires, optical fibers, or wirelessly such that electrical, optical, and/or electromagnetic signals may be exchanged between the components. It should be understood that other means of connecting the various components of the system not specifically described herein are included without departing from the scope of the present disclosure.

A "wound" generally refers to tissue injury on a subject, which may include an opening in the subject's skin or may include unbroken skin that exhibits other injury characteristics, such as a contusion, redness, or the like. A wound is generally susceptible to inflammation, infection, and/or the like. One example of a wound is an ulcer, such as a pressure ulcer. Pressure ulcers may occur, for example, as the result of a bedridden subject being stationary in bed for an extended period of time. Pressure ulcers may be divided into four classes based on their severity, including Stage I ulcers where the skin remains intact with non-blanching redness, Stage II ulcers where the ulcer is shallow and open and has a pinkish wound bed, Stage III ulcers where a full thickness tissue loss has occurred such that subcutaneous fat is visible, and Stage IV ulcers where a full thickness tissue loss has occurred such that muscle and/or bone is visible. While the device described herein may generally be aimed at a target area that includes a wound, it should be understood that other objects, such as surgical scars, lesions (e.g., moles), anatomical features surrounding the wound, and/or the like may also be imaged without departing from the scope of the present disclosure. In addition, the present disclosure references a "target object." It should be understood that when the device described herein is aimed at a wound, the target object may be the wound. As such, the terms "target object" and "wound" may be used interchangeably herein. In addition, the term "target area" refers to an imaged area as a whole, including the target object.

Figure 1B:
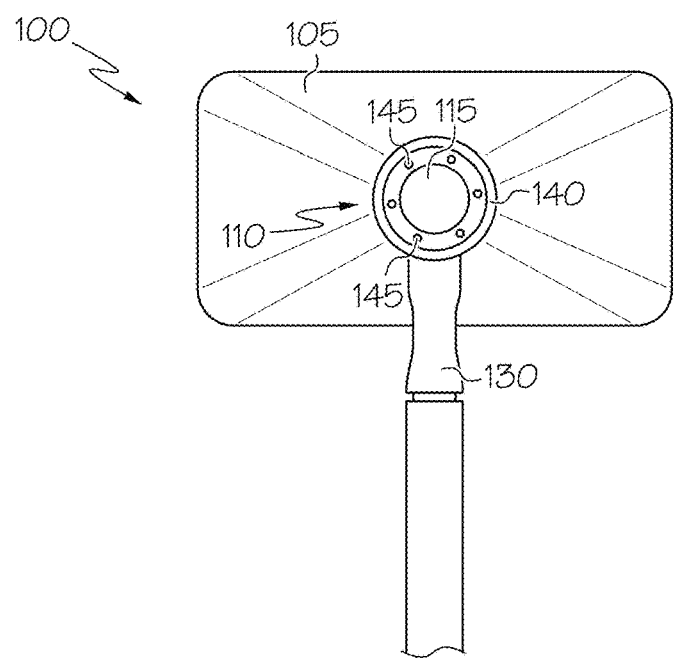
FIG. 1B depicts a front view of an illustrative pressure wound monitoring device according to one or more embodiments shown or described herein.

Referring to FIGS. 1A and 1B, a device 100 for determining characteristics of one or more wounds W on a subject S is depicted. The device 100, which may also be referred to herein as a monitoring device, includes a body 105 having an imaging component 110. In addition, the device 100 includes a computing device 120 communicatively coupled to the imaging component 110. The device 100 may also include a support 130 that supports the body 105 including the imaging component 110 and the computing device 120 and, in some embodiments, may couple the imaging component 110 and the computing device 120 together. For example, the support 130 may be a grip or the like that is held by a user when carrying and/or operating the device 100.

In some embodiments, the device 100 may further include one or more user interface components, such as, for example, a display 125 and/or a trigger 135. In some embodiments, the display 125 and/or the trigger 135 may be included as a portion of the computing device 120, as described in greater detail herein. The device 100 is generally arranged and configured such that the imaging component 110 is positioned to image a subject S and/or one or more wounds W on the subject and transmit data corresponding to images of the subject and/or one or more wounds to the computing device 120.

The device 100 may generally be a handheld device. As used herein, a "handheld device" generally refers to a device that is generally portable in nature such that it can be held and manipulated by a single user. As such, a handheld device may have dimensional characteristics (e.g., shape, size, etc.) that allow for holding and manipulation by a single user. Accordingly, the device 100 may be particularly configured and designed such that a single user such as the subject, a friend of the subject, a family member of the subject, a caretaker of the subject, other non-medical personnel, and/or the like can hold and manipulate the device 100 in a manner as described herein.

In some embodiments, the device 100 may be constructed of a plurality of modular components such that various components may be removed from the device 100 and/or coupled to the device 100. For example, in some embodiments, the computing device 120 may be removable from the device 100 and may further be used as a separate component (e.g., a mobile device such as a mobile phone or the like that contains software for carrying out the various processes described herein). As such, the device 100 may include one or more temporary fasteners, clips, and/or the like that allow for attachment or detachment of one or more components of the device 100, such as the computing device 120. The computing device 120 and/or the display 125 are arranged such that images that are received from the imaging component 110 and information and/or images are displayed to one or more individuals operating the device 100 when the device 100 is positioned to image a target object. Thus, at least one component of the computing device 120 (such as the display 125) may be arranged such that the one or more individuals operating the device 100 can view the displayed images I and/or information.

As depicted in FIGS. 1A and 1B, the imaging component 110 includes an imaging device 115, one or more light emitting components 140 and one or more laser emitting devices 145. The one or more light emitting components 140 and the one or more laser emitting devices 145 may generally be arranged and positioned such that the imaging device 115, the one or more light emitting components 140, and the one or more laser emitting devices 145 are all aimed in the same general direction. That is, the imaging device 115 may be positioned to image a target area that is illuminated by the one or more light emitting components 140 and/or receives a projection from the one or more laser emitting devices 145. For example, an optical axis A of the imaging device 115 extends towards at least a portion of a subject and/or one or more wounds thereon when aimed by a user. In the embodiments described herein, the optical axis A refers to an imaginary line defining the path along which electromagnetic radiation (such as light) propagates to and through the imaging device 115.

The imaging device 115 may be any imaging device, sensor, or detector that is suitable for obtaining images within any portion of the electromagnetic spectrum, such as, for example, the visible spectrum (e.g., radiation having a wavelength from about 390 nanometers (nm) to about 700 nm). As used herein, the term "images" or "image" refers video images (i.e., a sequence of consecutive images) and/or still images (including still images isolated from video images) that are captured by the imaging device 115. Any suitable commercially available imaging device may be used without departing from the scope of the present disclosure. In some embodiments, the imaging device 115 may be coupled to one or more other components that provide additional functionality for imaging, such as, for example, a thermal imaging device.

The imaging device 115 may include or may be coupled to a lens (not shown). The lens is not limited by this disclosure and may generally be any optical component that is configured to focus the light entering the imaging device 115 such that an image can be properly obtained. In some embodiments, the lens may be a fixed lens that is not adjustable. In other embodiments, the lens may be adjustable, either manually or automatically by the imaging component 110, to zoom in on an object, zoom out on an object, and/or adjust the focus of the light entering the imaging device 115.

While FIGS. 1A and 1B depict a single imaging device 115, it should be understood that any number of imaging devices 115 may be used in conjunction with the imaging component 110. For example, in some embodiments, the imaging component 110 may include two or more imaging devices 115. In some embodiments, the number of imaging devices 115 in the imaging component 110 may be sufficient to render a three dimensional (3D) image of a subject and/or one or more wounds thereon.

Each of the one or more light emitting components 140 may generally be a device or the like that is calibrated to emit light having particular characteristics. That is, the light emitted from the one or more light emitting components 140 may have a particular wavelength or the like. As such, the light emitted by the one or more light emitting components 140 is preset for the purposes of determining the color of the same light that is reflected from a target object. For example, the one or more light emitting components 140 may be one or more light emitting diode (LED) lights that emit light at one or more particular wavelengths (e.g., having a spectral distribution from about 185 nanometers (nm) to about 400 nm). The one or more light emitting components 140 may further be configured to be recalibrated to emit a different wavelength and/or may be periodically recalibrated to ensure that the light emitted from the one or more light emitting components 140 is consistent. An illustrative example of a light emitting component that may be used is the L7810-02 xenon lamp light source manufactured by Hamamatsu Photonics K. K (Hamamatsu, JP). While FIG. 1B depicts a single light emitting component 140 as a ring around the imaging device 115, this is merely an illustrative example. In other embodiments, a plurality of light emitting components 140 may be distributed at another location on the device 100, such as distributed at various locations around the imaging device 115.

Referring to FIG. 1B, each of the one or more laser emitting devices 145 may generally be a semiconductor laser diode or the like that outputs a beam of coherent light. For example, a laser emitting device 145 may be a semiconductor laser that outputs a beam of coherent visible light at any color. As used herein, the phrase "semiconductor laser" means any laser device having a semiconductor gain medium that can be pumped electrically or optically to produce a desired wavelength of light. Illustrative gain media include, but are not limited to, GaAs (gallium arsenide), AlGaAs (aluminum gallium arsenide), GaP (gallium phosphide), InGaP (indium gallium phosphide), GaN (gallium nitride), InGaAs (indium gallium arsenide), GaInNAs (indium gallium arsenide nitride), InP (indium phosphide), GaInP (gallium indium phosphide), and/or the like. Examples of semiconductor laser devices may include, but are not limited to, a Distributed Feedback (DFB) laser and a Distributed Bragg Reflector (DBR) laser. In addition, each of the one or more laser emitting devices 145 may be positioned relative to the imaging device 115 such that each of the laser emitting devices 145 projects the light beam generally towards an area imaged by the imaging device 115.

As shown in FIG. 1B, the one or more laser emitting devices 145 may be evenly distributed about a circumference of the imaging device 115. However, other locations for the one or more laser emitting devices 145 are contemplated and are included within the scope of the present disclosure. The one or more laser emitting devices 145 may be angled at a particular angle relative to a surface of the device 100. As a result, the light emitted from each of the one or more laser emitting devices 145 is a fan beam projected at the particular angle relative to the surface of the device 100, which produces a laser line on a surface located a distance away from the device 100 and is in the general direction in which portions of the device 100 (e.g., the imaging device 115, the one or more light emitting components 140, and the one or more laser emitting devices 145) are aimed.

A switching mechanism in the imaging component 110 may control activation or deactivation of the one or more light emitting components 140 and/or the one or more laser emitting devices. That is, the one or more light emitting components 140 and/or the one or more laser emitting devices 145 may be switched by the switching mechanism when a control signal is received by the switching mechanism. In some embodiments, switching may occur such that the one or more light emitting components 140 and the one or more laser emitting devices 145 can be activated or deactivated independently from one another. In other embodiments, switching of one of the devices may directly affect switching of the other devices. That is, the one or more laser emitting devices 145 may only be switched to an active state (emitting light) only when the one or more light emitting components 140 is switched off, so as to avoid a situation where the light emitted from the one or more light emitting components 140 "washes out" the light emitted from the one or more laser emitting devices 145 (laser light), making the laser light difficult to see. Similarly, the one or more light emitting components 140 may only be switched to an active state (emitting light) only when the one or more laser emitting devices 145 are switched off, so as to avoid a situation where the laser light contaminates the calibrated color of the light emitted from the light emitting components 140, which could cause an incorrect color measurement of the reflected light.

While FIG. 1B depicts the one or more light emitting components 140 being devices that are separate from the one or more laser emitting devices 145, this is merely illustrative. That is, in some embodiments, one or more devices that are configured to emit both laser light and calibrated light may be used in lieu of the one or more light emitting components 140 and the one or more laser emitting devices 145. For example, a device 100 that incorporates both LED units and laser diodes in the same housing may be used.

Referring again to FIGS. 1A-1B, certain components of the device 100 are communicatively coupled to each other to transmit data. For example, the computing device 120 is communicatively coupled to the imaging component 110 such that the computing device 120 receives data transmissions, particularly data transmissions containing image data, from the imaging component 110. In some embodiments, the imaging component 110 and the computing device 120 may be connected via a network. The network may include a wide area network (WAN), such as the Internet, a local area network (LAN), a mobile communications network, a public service telephone network (PSTN), a personal area network (PAN), a metropolitan area network (MAN), a virtual private network (VPN), a mesh network, or any other suitable network. In other embodiments, the imaging component 110 and the computing device 120 may be directly connected to one another. In addition, the imaging component 110 and the computing device 120 may be communicatively connected to one another via any means of wireless or wired communication, such as, but not limited to one or more wires, cables, and/or the like, one or more wireless radios such as, for example, a Bluetooth radio, an 802.11 standard radio, a near field communication (NFC) radio, a radio frequency (RF) radio, and/or the like.

Figure 2A:
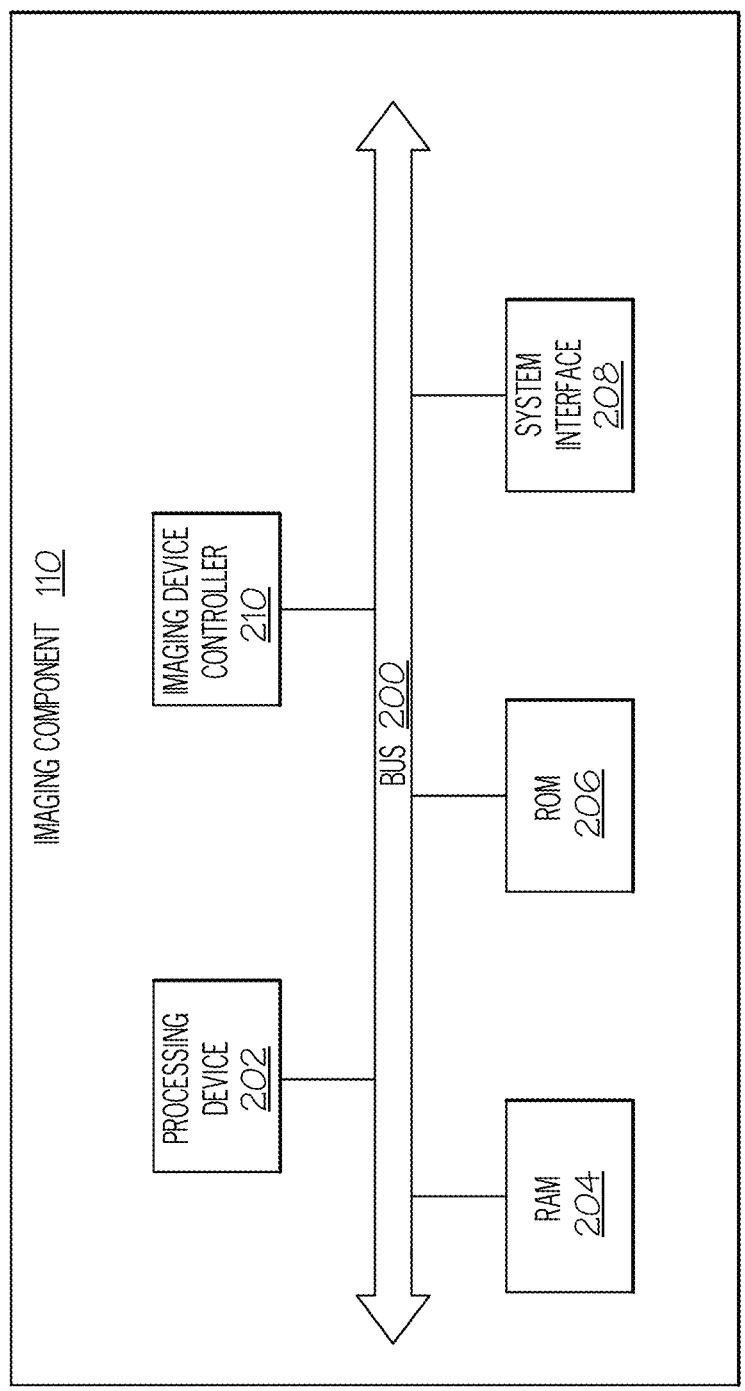
FIG. 2A schematically depicts a block diagram of illustrative internal components of a imaging component in a pressure wound monitoring device according to one or more embodiments shown or described herein.
Figure 2B:
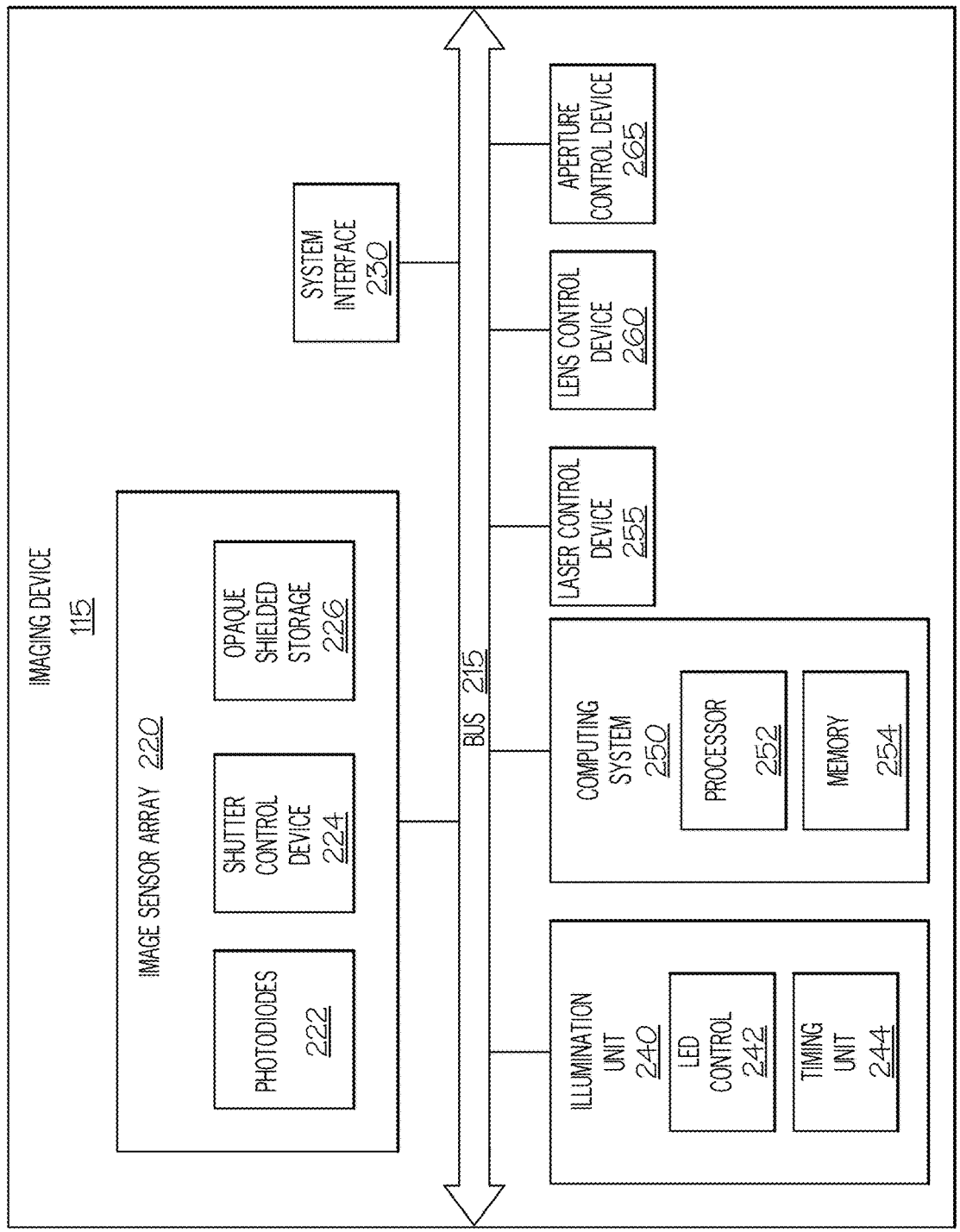
FIG. 2B schematically depicts a block diagram of illustrative internal components of an imaging device in a imaging component of a pressure wound monitoring device according to one or more embodiments shown or described herein.

In order for the imaging component 110 to function as described herein (e.g., for the imaging device 115 to obtain images, the one or more light emitting components 140 to emit light at a calibrated wavelength, the one or more laser emitting devices 145 to emit a laser projection, and/or the like), the imaging component 110 may further include a plurality of hardware components. Referring also to FIG. 2A, various illustrative hardware components of the imaging component 110 are depicted. A bus 200 may interconnect the various components. A processing device 202, such as a computer processing unit (CPU), may be the central processing unit of the imaging component 110, performing calculations and logic operations required to execute a program. The processing device 202, alone or in conjunction with one or more of the other elements disclosed in FIGS. 2A and 2B, is an illustrative processing device, computing device, processor, or combination thereof, as such terms are used in this disclosure.

Still referring to FIGS. 1A-1B and 2A, memory, such as read only memory (ROM) 206 and random access memory (RAM) 204, may constitute illustrative memory devices (i.e., non-transitory, processor-readable storage media). Such memory 204, 206 may include one or more program instructions thereon that, when executed by the processing device 202, cause the processing device 202 to complete various processes, such as the processes described herein. Optionally, the program instructions may be stored on a tangible computer-readable medium such as a digital disk, flash memory, a memory card, a USB drive, an optical disc storage medium (e.g., Blu-Ray™, CD, DVD), and/or other non-transitory processor-readable storage media.

A system interface 208 may generally provide the imaging component 110 with an ability to interface with one or more external devices, particularly one or more portions of the device 100, such as the computing device 120, as described in greater detail herein. Communication with such external devices may occur using various communication ports (not shown). An illustrative communication port may be attached to a communications network.

An imaging device controller 210 may generally provide the imaging component 110 with an ability to control the imaging device 115. For example, the imaging device controller 210 may provide control signals to the imaging device 115 and/or components thereof for the purposes of obtaining an image, transmitting image data, and/or the like, as described in greater detail herein.

To obtain images and provide data relating to the images to the computing device 120, the imaging device 115 also includes a plurality of hardware components. Referring to FIGS. 1A-1B and 2B, various illustrative hardware components of the computing device 120 are depicted. A bus 215 may interconnect the various components, including, but not limited to, an image sensor array 220, a system interface 230, an illumination unit 240, a computing system 250 having a processor 252 and a memory 254, a laser control device 255, a lens control device 260, and an aperture control device 265.

The image sensor array 220 may generally be any commercially available image sensor array, such as, for example, a charge-coupled device (CCD) or an active pixel sensor in a complementary metal-oxide semiconductor (CMOS) or N-type metal-oxide semiconductor (NMOS) array. As such, it should be understood that the image sensor array 220 may be constructed of a plurality of rows and columns of pixels. For example, the image sensor array 220 may be arranged as a grid having about 1500 pixels by about 1152 pixels, about 1280 pixels by about 1024 pixels, or about 640 pixels by about 480 pixels. In some embodiments, a size of each pixel in the image sensor array 220 may be such that the length and width of each pixel is about 6 micrometers (μm) by about 6 μm, about 4 μm by about 4 μm, about 2 μm by about 2 μm, about 1 μm by about μm, or the like.

Each of the pixels of the image sensor array 220 may include various other components that allow the pixels to receive and process light reflected by a target object, such as a wound. Illustrative components may include, for example, a plurality of photodiodes 222, a shutter control device 224, and opaque shielded storage 226. Each of the plurality of photodiodes 222 includes a light-receiving surface having a substantially uniform length and width. During exposure, the each of the plurality of photodiodes 222 converts the incident light to a charge. The shutter control device 224 initiates exposure of the photodiodes 222 and terminates exposure of the photodiodes 222. In some embodiments, after the photodiodes 222 are exposed, a charge is transferred from the photodiodes 222 to the opaque shielded storage 226. In addition, the shutter control device 224 also controls resetting of the photodiodes 222 and an output of the stored charges to be processed by the computing system 250. In some embodiments, a single shutter control device 224 may control each of the plurality of photodiodes 222. As such, the shutter control device 224 is configured to operate the image sensor array 220 as a global shutter. That is, substantially all of the photodiodes 222 are exposed simultaneously and for substantially identical lengths of time. The global exposure effectively integrates charge substantially evenly across the image sensor array 220 during the exposure time. In other embodiments, a plurality of shutter control devices 224 may control the plurality of photodiodes 222 (e.g., each of the plurality of photodiodes 222 is coupled to a corresponding one of the plurality of shutter control devices 224).

In some embodiments, the opaque shielded storage 226 may be omitted from the image sensor array 220. Instead, a CMOS sensor with a global reset mode may be used.

In some embodiments, the image sensor array 220 may be configured such that exposure of the photodiodes 222 in the image sensor array 220 can be initiated and terminated automatically, in response to a user input, or a combination thereof. The image sensor array 220 may further be configured such that the exposure period (i.e., the amount of time one or more of the photodiodes 222 is exposed to light) is adjustable or fixed.

The illumination unit 240 may generally be a component that controls illumination of the one or more light emitting components 140. In addition, the illumination unit 240 may be a component that coordinates illumination of the one or more light emitting components 140 with a timing and exposure of the image sensor array 220. As such, the illumination unit 240 includes an LED control unit 242 and a timing unit 244. The LED control unit 242 may generally be any controller that transmits signals to the one or more light emitting components 140 or the switching mechanism to cause the light emitting components 140 to illuminate (turn on) or extinguish (turn off). In some embodiments, the LED control unit 242 may transmit signals to the one or more light emitting components 140 to cause the one or more light emitting components 140 to emit light having particular characteristics. That is, the LED control unit 242 may be configured to transmit a signal to the one or more light emitting components 140 to emit light at a particular wavelength or the like so as to ensure that a color of the light reflected by the target object (e.g., the wound) can be accurately determined, as described in greater detail herein.

The timing unit 244 may generally be any timing device that functions in conjunction with the LED control unit 242 to ensure that the one or more light emitting components 140 are illuminated or extinguished for a particular period of time. While FIG. 2B depicts the timing unit 244 as being a component of the illumination unit 240, it should be understood that this is a nonlimiting example. That is, the timing unit may also be a separate component that includes a processor and a memory that is operatively coupled to the computing system 250 and/or the image sensor array 220. In some embodiments, the timing unit 244 may be a computer program that is stored in the memory 254 of the computing system 250 and configured to be run by the processor 252 of the computing system 250.

The timing unit 244 can be configured in conjunction with the LED control unit 242 to direct the one or more light emitting components 140 to illuminate at a time just before the image sensor array 220 initiates a shutter exposure and to cease illumination shortly after the shutter exposure ends. In other embodiments, the timing unit 244 can be configured in conjunction with the LED control unit 242 to direct the one or more light emitting components 140 to illuminate after the shutter exposure begins and to cease illumination before the shutter exposure ends. In another embodiment, the timing unit 244 can be configured in conjunction with the LED control unit 242 to direct the one or more light emitting components 140 to illuminate with an overlap period of time with the shutter exposure period of time. In some embodiments, the timing unit 244 can be configured in conjunction with the LED control unit 242 to direct the one or more light emitting components 140 to pulse or produce a strobe-like light during the illumination period.

The computing system 250 includes the processor 252 communicatively coupled to the memory 254. The processor 252, such as a computer processing unit (CPU) or the like, may be the central processing unit of the computing system 250 and the imaging device 115, performing calculations and logic operations required to execute a program. The processor 252, alone or in conjunction with one or more of the other elements disclosed in FIGS. 2A and 2B, is an illustrative processing device, computing device, processor, or combination thereof, as such terms are used in this disclosure. In some embodiments, the processor 252 may be integrated with the processing device 202 of the imaging component 110 (FIG. 2A). In other embodiments, the processing device 202 of the imaging component 110 (FIG. 2A) may complete all of the processing functions of the imaging device 115 described herein in lieu of the processor 252.

Still referring to FIGS. 1A-1B and 2B, memory 254, such as ROM and RAM, may constitute illustrative memory devices (i.e., non-transitory, processor-readable storage media). Such memory 254 may include one or more program instructions thereon that, when executed by the processor 252, cause the processor 252 to complete various processes, such as the processes described herein. Optionally, the program instructions may be stored on a tangible computer-readable medium such as a digital disk, flash memory, a memory card, a USB drive, an optical disc storage medium (e.g., Blu-Ray™, CD, DVD), and/or other non-transitory processor-readable storage media. In some embodiments, the memory 254 may be integrated with the RAM 204 and/or the ROM 206 of the imaging component 110 (FIG. 2A). In other embodiments, the RAM 204 and/or the ROM 206 of the imaging component 110 (FIG. 2A) may store the program instructions that are executed by the processor 252 in lieu of the memory 254.

Still referring to FIGS. 1A-1B and 2B, the system interface 230 may generally provide the imaging device 115 with an ability to interface with one or more other components of the imaging component 110, such as the system interface 208 in the imaging component 110 (FIG. 2A). Communication with such other components may occur using various communication ports (not shown).

The laser control device 255 may generally be any controller that transmits signals to the one or more laser emitting devices 145 or the switching mechanism to cause the one or more laser emitting devices 145 to illuminate (turn on) or extinguish (turn off). That is, the laser control device 255 may transmit one or more signals to the one or more laser emitting devices 145 to cause the one or more laser emitting devices 145 to emit a laser line that is used to ensure that a target object such as a wound is located within a focal range of the imaging device 115 such that an image of the target object can be appropriately captured, as described in greater detail herein.

The lens control device 260 may generally be any controller that transmits signals to one or more lens portions of the imaging component 110 to cause the one or more lens portions to move, such as to focus on a target object such as a wound and/or to zoom in or out on the target object. That is, the lens control device 260 may be particularly configured to provide signals to a lens that causes the lens to focus the light incident on the image sensor array 220 and/or focus light that is emitted by the one or more light emitting components 140.

The aperture control device 265 may generally be any controller that transmits signals to one or more aperture portions of the imaging component 110 to cause the one or more aperture portions to move, such as to control an amount of light that is passed through the aperture portions. That is, the aperture control device 265 may be particularly configured to provide signals to an aperture that causes the aperture to open or close.

In the embodiments described herein, the computing device 120 is a computer that receives images in the form of image data, processes the image data, and provides information. In some embodiments, the computing device 120 may be particularly configured to process image data and determine characteristics of a wound by using specific components not commonly included in a general purpose computer. For example, in some embodiments, various components of the computing device 120 may be integrated with one or more of the components of the imaging component 110. That is, at least a portion of the imaging component 110 and at least one component of the computing device 120 may be particularly integrated to obtain and process images specifically for the purpose of determining characteristics of a wound.

Figure 2C:
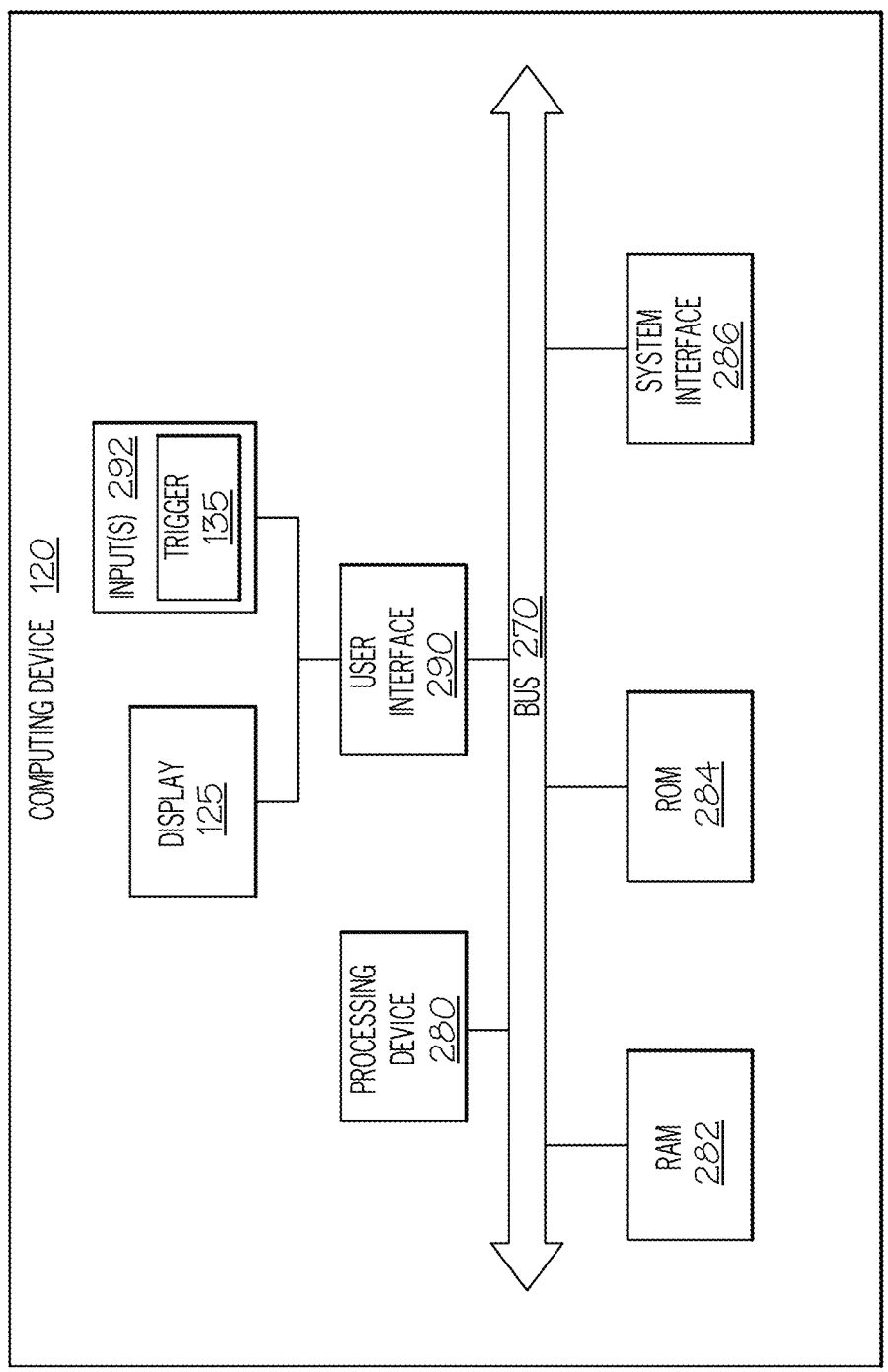
FIG. 2C schematically depicts a block diagram of illustrative internal components of a computing device in a pressure wound monitoring device according to one or more embodiments shown or described herein.

Referring again to FIGS. 1A-1B, to receive the image data, process the images, determine characteristics of wound based on images thereof, and provide information, the computing device 120 includes a plurality of hardware components. Referring also to FIG. 2C, various illustrative hardware components of the computing device 120 are depicted. A bus 270 may interconnect the various components. A processing device 280, such as a computer processing unit (CPU), may be the central processing unit of the computing device 120, performing calculations and logic operations required to execute a program. The processing device 280, alone or in conjunction with one or more of the other elements disclosed in FIG. 2C, is an illustrative processing device, computing device, processor, or combination thereof, as such terms are used within this disclosure. Memory, such as read only memory (ROM) 284 and random access memory (RAM) 284, may constitute illustrative memory devices (i.e., non-transitory, processor-readable storage media). Such memory 282, 284 may include one or more program instructions thereon that, when executed by the processing device 280, cause the processing device 280 to complete various processes, such as the processes described herein. Optionally, the program instructions may be stored on a tangible computer-readable medium such as a digital disk, flash memory, a memory card, a USB drive, an optical disc storage medium, such as a Blu-Ray™ disc, a digital versatile disc (DVD) a compact disc (CD), and/or other non-transitory processor-readable storage media.

An optional user interface 290 may permit information from the bus 270 to be displayed on the display 125 in audible, visual, graphic, or alphanumeric format. The user interface 290 may also include one or more inputs 292 that allow for transmission to and receipt of data from input devices such as a keyboard, a mouse, a joystick, a touch screen, a remote control, a pointing device, a video input device, an audio input device, a haptic feedback device, the trigger 135, and/or the like. In some embodiments, the display 125 and one or more of the inputs 292 may be combined into a single device, such as a touchscreen display or the like. Such a user interface 290 may be used, for example, to allow a user to view images of the subject and/or the wounds thereon, view information regarding focus of the image, receive instructions for adjusting the positioning of the device 100, provide inputs for capturing the image, provide instructions for transmitting image data, wound characteristic data, scoring data, and/or the like.

A system interface 286 may generally provide the computing device 120 with an ability to interface with one or more external devices, particularly the one or more other portions of the device 100, such as, for example, the imaging component 110. Communication with external devices may occur using various communication ports (not shown). An illustrative communication port may be attached to a communications network.

Figure 3:
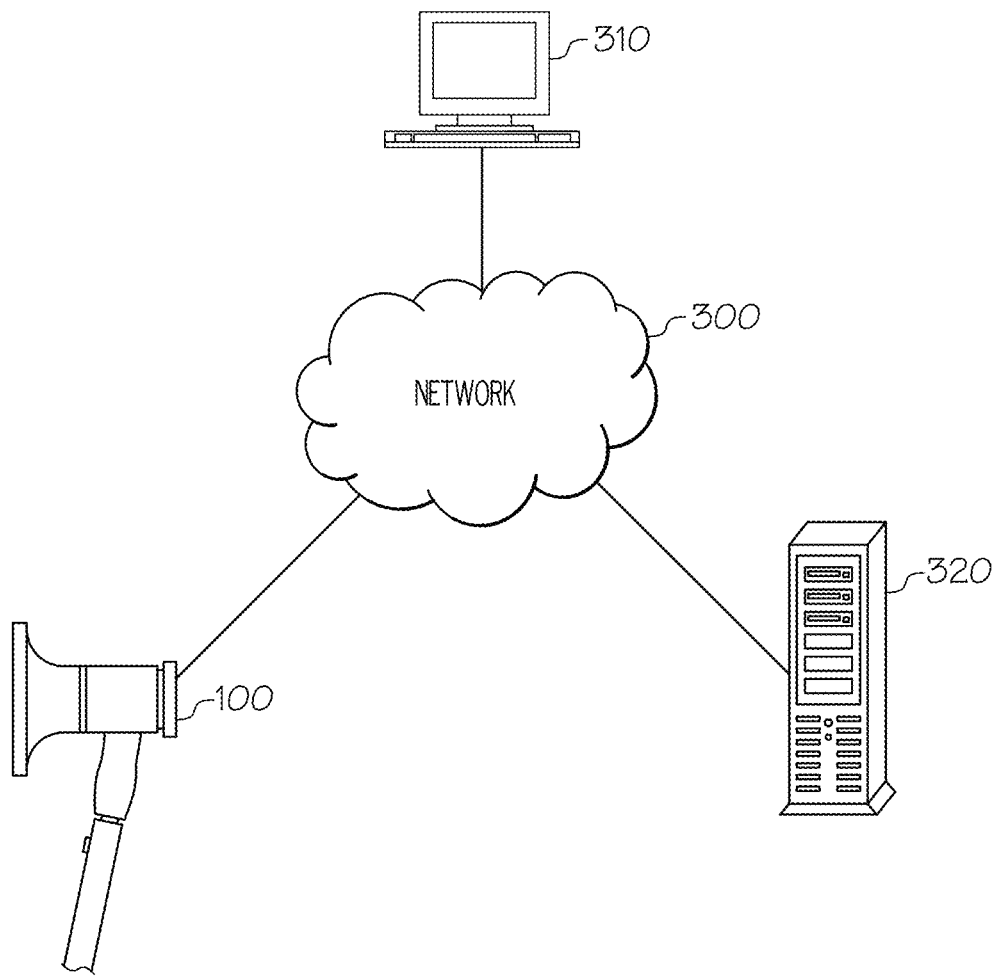
FIG. 3 schematically depicts an interconnectivity of the various components of a pressure wound monitoring system according to one or more embodiments shown or described herein.

Referring to FIG. 3, to provide an ability to transmit image data, analysis data, and/or the like, the device 100 may be coupled to one or more external devices in some embodiments. For example, as depicted in FIG. 3, the device may be communicatively coupled to one or more of a user computing device 310 and a server computing device 320 via a network 300. The network 300 may include a wide area network (WAN), such as the Internet, a local area network (LAN), a mobile communications network, a public service telephone network (PSTN), a personal area network (PAN), a metropolitan area network (MAN), a virtual private network (VPN), a mesh network, or any other suitable network.

The user computing device 310 may generally be used as an interface between a user and the other components connected to the network 300, such as the device 100. Thus, the user computing device 310 may be used to perform one or more user-facing functions, such as receiving one or more inputs from a user or providing information to the user, as described in greater detail herein. Accordingly, the user computing device 310 may include at least a display and/or input hardware. In the event that the server computing device 320 requires oversight, updating, or correction, the user computing device 310 may be configured to provide the desired oversight, updating, and/or correction. The user computing device 310 may also be used to input additional data into a corpus of data stored on the server computing device 320. For example, if a user of the user computing device 310 is medical personnel reviewing images and results of a determination made by the device 100, the medical personnel may enter data regarding a diagnosis, a prescription, a recommendation, and/or the like that is stored on the server computing device 320 together with any data that is transmitted by the device 100.

The server computing device 320 may receive data from one or more sources, generate data, store data, index data, search data, and/or provide data to the user computing device 310 and/or the device 100 in the form of a software program, results of a query, medical records, historical image data, and/or the like.

It should be understood that while the user computing device 310 is depicted as a personal computer and the server computing device 320 is depicted as a server, these are nonlimiting examples. More specifically, in some embodiments, any type of computing device (e.g., mobile computing device, personal computer, server, etc.) may be used for any of these components. Additionally, while each of these computing devices is illustrated in FIG. 3 as a single piece of hardware, this is also merely an example. More specifically, each of the user computing device 310 and the server computing device 320 may represent a plurality of computers, servers, databases, components, and/or the like.

The various processes that may be carried out by the device 100 in obtaining image data from the imaging component 110, determining a wound from the image data, determining a size of the wound, determining a tissue type of the wound, determining an amount of exudate from the wound, scoring the wound based on characteristics such as the size, the tissue type, and/or the amount of exudate, and/or monitoring the progress of the wound is depicted in the flow diagrams of FIGS. 4 and 8-10. Each of the processes described with respect to FIGS. 4 and 8-10 may be embodied by one or more programmed instructions stored on one or more memory devices, such as the RAM 282 or the ROM 284 (FIG. 2C) described herein. It should be understood that while the processes described with respect to FIGS. 4 and 8-10 are described herein independently, such processes may be completed in conjunction with one another without departing from the scope of the present disclosure. That is, the computing device 120 may determine the size of the wound, the type of tissue, and the amount of exudate during the same imaging process such that some of the steps described herein with respect to FIGS. 4 and 8-10 are only completed a single time instead of for each characteristic of the wound. For example, processes relating to receiving a user input, activating the one or more light emitting components, activating the one or more laser emitting devices, determining if the image is focused, receiving an image, transmitting data, and/or determining whether additional imaging is necessary may be completed once and used for one or more of the characteristics of the wound described herein so as to avoid redundant processes.

Prior to beginning the processes described with respect to FIGS. 4 and 8-10, a user may activate the device 100 and prepare the device for imaging a target object, such as a wound. That is, prior to capturing an image of a wound W, a user may position the device 100 such that the device is aimed at the wound W and the wound W appears in a field of view F of the device, as shown in FIG. 1A. For example, if a pressure wound W on a posterior of a subject S is to be imaged, the device 100 may be aimed such that the imaging component 110 is facing the pressure wound W. In addition, the device 100 may also be aimed such that the display 125 is viewable by the user of the device. Accordingly, the user may view a "live view" of the images I obtained by the imaging component 110 to determine if the device 100 is appropriately aimed at the pressure wound W or if the device 100 is in need of repositioning. In addition to activating, preparing, and positioning the device 100, the user may also tag or otherwise identify the wound W to be imaged such that the wound W can be subsequently identified for later additional monitoring, as described herein. Tagging is not limited by the present disclosure, and may be completed in any manner. For example, a user may enter, via a user interface provided by the display 125, information relating to the identification of the wound, such as the location of the wound W (e.g., "left shoulder blade," "small of back," "right triceps," etc.). Such information may be stored for later access so that the wound W can be identified by the user or the computing device 120 for subsequent imaging.

The user of the device 100 may generally be any individual. In particular embodiments, the user of the device 100 may be an individual that is assisting the subject with the wound at a location that is away from a medical facility (e.g., at the subject's home, nursing home room, or the like). That is, the user may be an individual that is non-medical personnel.

Figure 4:
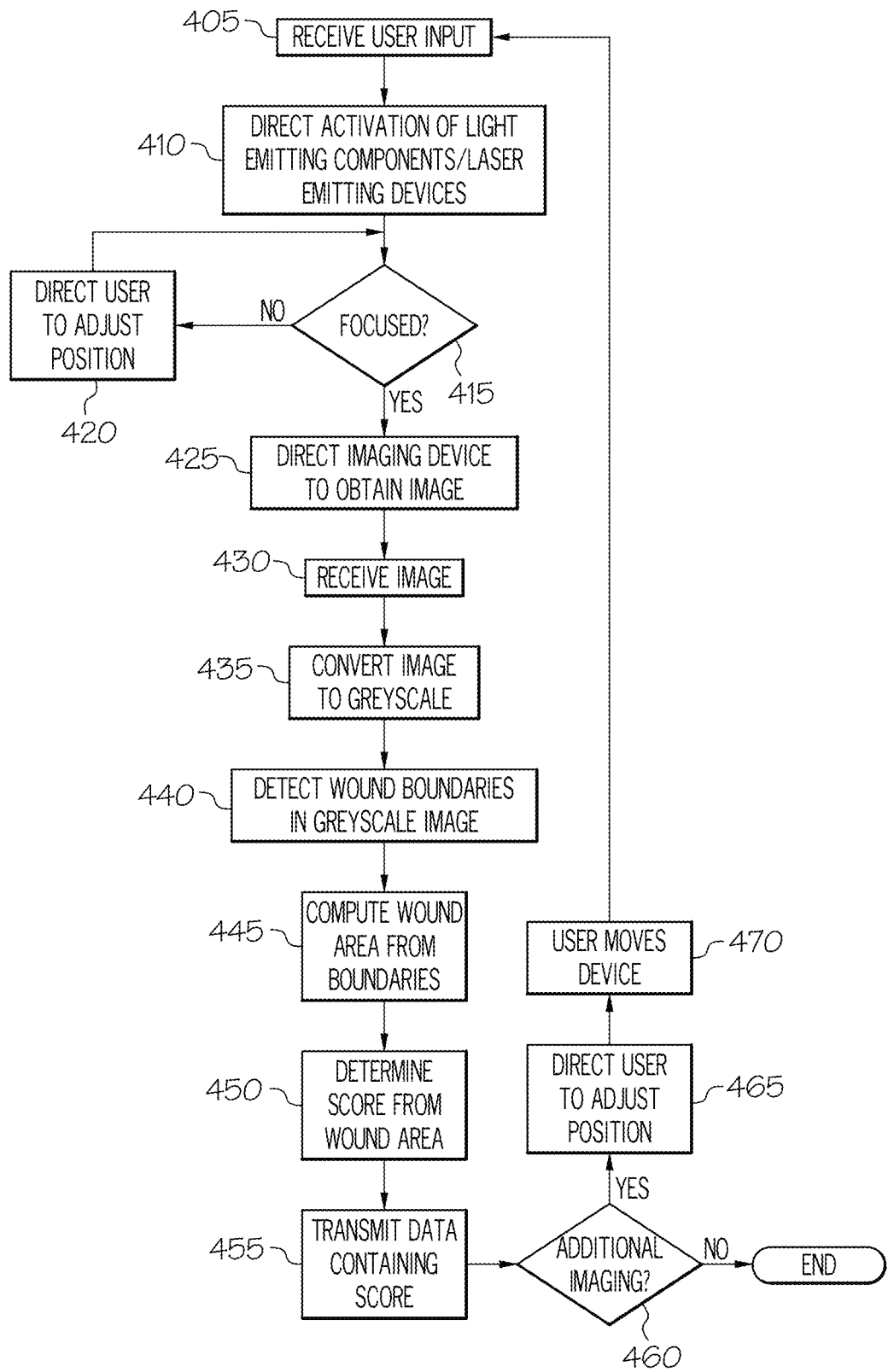
FIG. 4 depicts a flow diagram of an illustrative method of determining a wound size according to one or more embodiments shown or described herein.

Referring to FIGS. 1A-1B and 4, at step 405, the computing device 120 may receive a user input to begin imaging. For example, the user may depress the trigger 135 to begin imaging. It should be understood that step 405 is optional. That is, in some embodiments, the computing device 120 may not receive a user input to begin imaging. For example, the computing device 120 may recognize when a wound is within the field of view of the imaging device 115 and begin imaging, or the computing device 120 may be in an "always on" state when powered on such that it is ready to complete the various processes described with respect to FIG. 4 without any user input.

In some embodiments, the computing device 120 may direct the one or more light emitting components 140 to emit the calibrated light to illuminate the target object for imaging and/or direct the one or more laser emitting devices 145 to project a laser towards the target object to ensure that the device 100 is appropriately positioned with respect to the target object at step 410. For example, the computing device 120 may transmit a signal to the imaging component 110 to cause the imaging component 110 to direct the one or more light emitting components 140 to emit light at a particular wavelength. In another example, the computing device 120 may transmit a signal to the imaging component 110 to cause the imaging component 110 to direct the one or more laser emitting devices 145 to project a laser. In some embodiments, the computing device 120 may transmit a signal to the imaging component 110 to cause the imaging component 110 to first direct the one or more laser emitting devices 145 to project a laser, and then subsequently direct the one or more light emitting components 140 to project the calibrated light and correspondingly deactivate the laser emitted from the one or more laser emitting devices 145.

Figure 5:
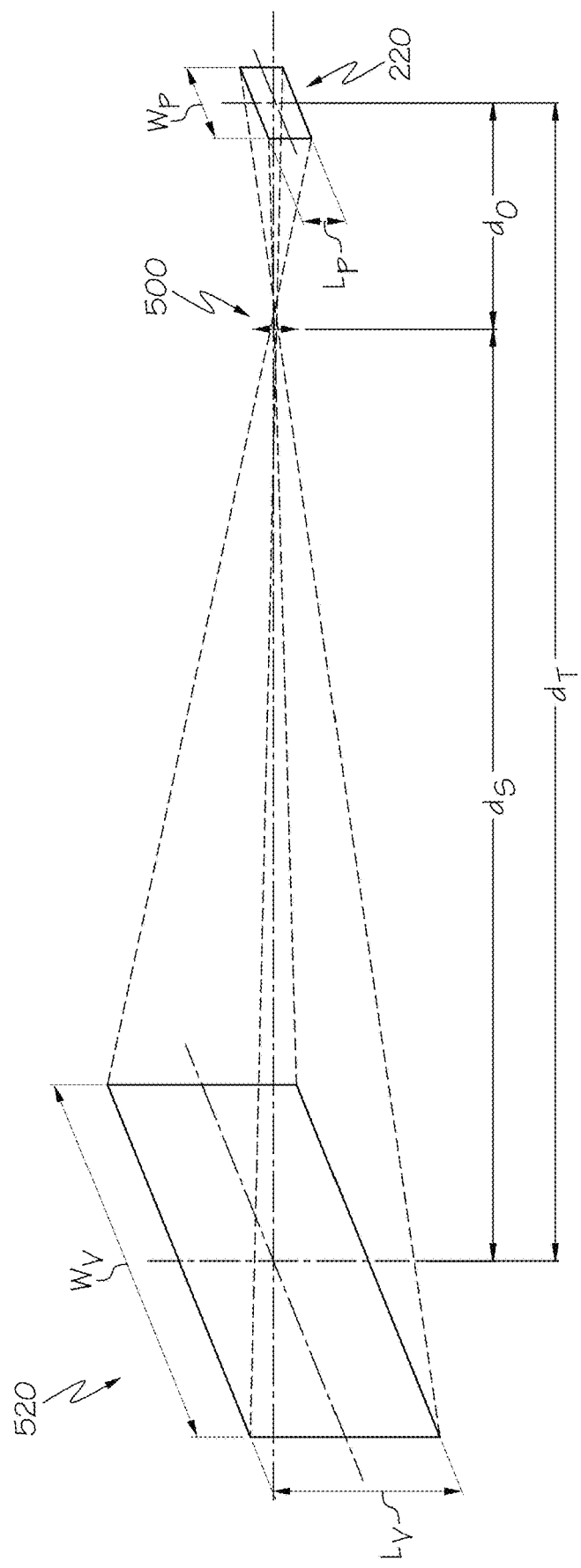
FIG. 5 schematically depicts an optical system of a pressure wound monitoring device when aimed at a target object according to one or more embodiments shown or described herein.

Accordingly, at step 415, a determination may be made as to whether the device 100 is appropriately positioned such that the image of the target object in the imaging component 110 is focused. As previously described hereinabove, the one or more laser emitting devices 145 may be utilized to ensure that the device 100 is positioned at a particular distance from the target object (e.g., the wound) to ensure that the target object is appropriately focused for imaging and an accurate measurement of the size of the target object is obtained. For example, FIG. 5 depicts a total distance $d_T$ between the image sensor array 220 and an area of view 520 when a lens 500 coupled to the image sensor array 220 is located a focal length $d_0$ from the image sensor array 220 and a distance $d_S$ from the area of view 520. The length $L_P$ and the width $W_P$ of the image sensor array 220 and the focal length $d_0$ are generally known because of the components included within the imaging component 110. For example, the length $L_P$ of the image sensor array 220 may be about 3.6 millimeters (mm) and contain 960 pixels, and the width $W_P$ of the image sensor array 220 may be about 4.8 mm and may contain about 1280 pixels. In addition, the image sensor array 220 may be coupled to a lens 500 having a focal length of about 11.2 mm, for example. Using the respective lengths of the image sensor array 220 and the area of view 520, the distance $d_S$ may be determined using Equation (1) below:

$$\frac{(L_P)}{d_0} = \frac{(L_V)}{d_s} \qquad (1)$$

When the area of view 520 has a length $L_V$ of about 100 mm, using Equation (1) above results in a distance $d_S$ of about 311.1 mm. Since the total distance $d_T$ is the sum of the distance $d_S$ and the focal length $d_0$, the total distance $d_T$ may be about 311.1 mm+11.2 mm=322.3 mm.

Figure 6A:
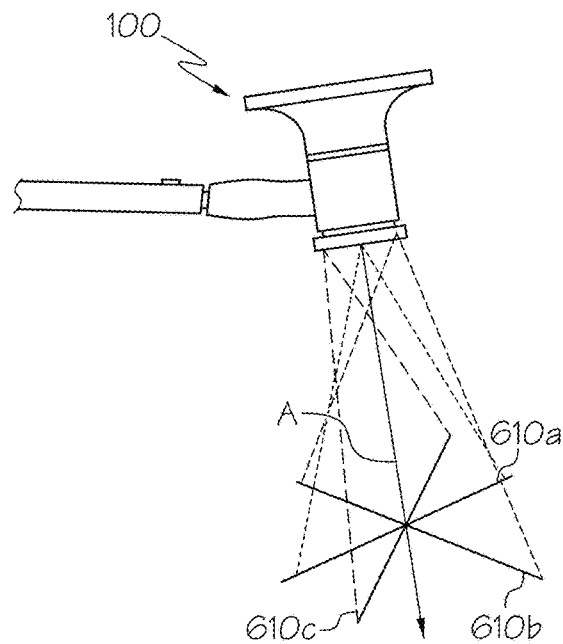
FIG. 6A schematically depicts illustrative laser beam projections from a pressure wound monitoring device according to one or more embodiments shown or described herein.
Figure 6B:
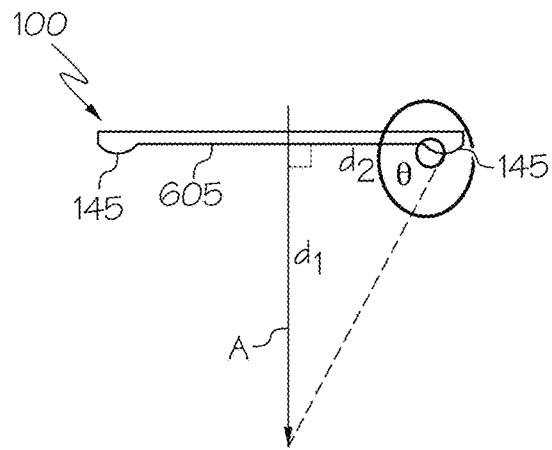
FIG. 6B schematically depicts a side view of an optical axis formed from the laser beam projections of FIG. 6A according to one or more embodiments shown or described herein.
Figure 6C:
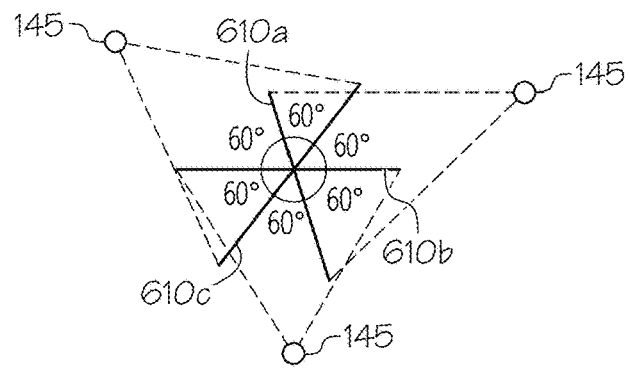
FIG. 6C schematically depicts a top view of an optical axis formed from the laser beam projections of FIG. 6A according to one or more embodiments shown or described herein.

In addition, the total distance $d_T$ may be used as a basis for the positioning and arrangement of the one or more laser emitting devices 145 such that, when the device 100 is positioned at a distance corresponding to the total distance $d_T$, the lasers projected from the laser emitting device may project a pattern that may be recognizable to a user as being indicative of an appropriate positioning of the device relative to the target object. For example, as depicted in FIG. 6A-6C, a plurality of laser lines 610a, 610b, 610c may be emitted by the one or more laser emitting devices 145. That is, each one of the one or more laser emitting devices 145 may emit a laser fan beam that results in a corresponding one of the plurality of laser lines 610a, 610b, 610c. In addition, each of the one or more laser emitting devices 145 may be particularly positioned such that it projects a laser fan beam at a particular angle Θ with respect to a surface 605 of the device 100 supporting the laser emitting device 145. The angle Θ may be selected, for example, such that the laser fan beam emitted therefrom results in a corresponding one of the plurality of laser lines 610a, 610b, 610c extending through an optical axis A of the device 100 at a particular distance $d_1$ that represents a distance in which the target object will be in focus when imaged and such that the distance between the device 100 and the target object is known so that the dimensional aspects of the target object can be accurately determined, which may be substantially equal to the distance $d_S$ described herein with respect to FIG. 5.

Still referring to FIGS. 6A-6C, when a plurality of fan beams are emitted by the one or more laser emitting devices 145 that are each particularly positioned and angled with respect to the surface 605 of the device 100, they result in the plurality of laser lines 610a, 610b, 610c that intersect at the optical axis A of the device 100 at the particular distance $d_1$, as particularly shown in FIGS. 6A and 6C. As such, a user may utilize the plurality of laser lines to position the device 100 appropriately by moving the device relative to the target object until the laser lines 610a, 610b, 610c intersect accordingly. If the laser lines 610a, 610b, 610c do not intersect as shown in FIGS. 6A and 6C, it may be used as an indication that the device 100 is located too close to the target object or too far away from the target object. Such an indicator may be used by the user or may be programmed such that the computing device 120 analyzes an image with the laser lines 610a, 610b, 610c and determines whether the laser lines intersect appropriately. If the intersection of the laser lines 610a, 610b, 610c is not positioned over the target object, the user may also reposition the device 100 such that the intersection of the laser lines 610a, 610b, 610c is located over the target object, which may optionally be in response to a direction from the computing device 120 to reposition the device 100.

It should be understood that while FIGS. 6A and 6C depict three laser emitting devices 145 emitting a corresponding three laser lines 610a, 610b, 610c, this is merely illustrative. That is, a number of laser emitting devices 145 greater than three may be used to emit more than three laser lines 610a, 610b, 610c without departing from the scope of the present disclosure. In addition, any number of laser emitting devices 145 may further be utilized to emit laser beams in other patterns and/or at other angles that can be utilized to determine whether the device 100 is appropriately positioned relative to the target object without departing from the scope of the present disclosure.

Referring again to FIGS. 1A-1B and 4, if the device 100 is not appropriately positioned, resulting in an unfocused image of the target object, the process may proceed to step 420 whereby the user is directed to adjust the positioning of the device 100. For example, the display 125 may display a user interface that provides instructions to the user to particularly position the device 100, such as by providing a diagram or the like indicating how the laser lines 610a, 610b, 610c described herein with respect to FIG. 6 are to be aligned by adjusting the location and/or positioning of the device 100 relative to the target object. The process may repeat at step 415 until the device 100 is appropriately positioned with respect to the target object.

If the device 100 is appropriately positioned to receive a focused image, the computing device 120 may direct the imaging device 115 to obtain the image at step 425. For example, the computing device 120 may direct the imaging device 115 by transmitting a signal to the imaging device 115 or transmitting a signal to the imaging component 110, which then directs the imaging device 115. It should be understood that step 425 is optional. That is, in some embodiments, the imaging device 115 may obtain images and/or transmit data without direction from the computing device 120. For example, the imaging device 115 may automatically obtain images and/or transmit data when powered on.

At step 430, the computing device 120 receives the image from the imaging device 115 via the imaging component 110. The image may be in the form of image data. Thus, the image may be transmitted as image data from the imaging device 115 to the computing device 120 via the imaging component 110. The computing device 120 converts the image, which may be an RGB image, to a greyscale image at step 435. For example, the computing device 120 may average the values of the red value, the green value, and the blue value in each pixel to obtain a greyscale value for that pixel and recolor the image based on the obtained greyscale values. In addition, conversion of the image to a greyscale image according to step 435 may be completed using any image processing software now known or later developed that provides greyscale conversion capabilities. One illustrative example of such an image processing software is the Parallel Computing Toolbox™ that is available as a portion of the MATLAB® application programming (Mathworks, Natick Mass.).

Figure 7A:
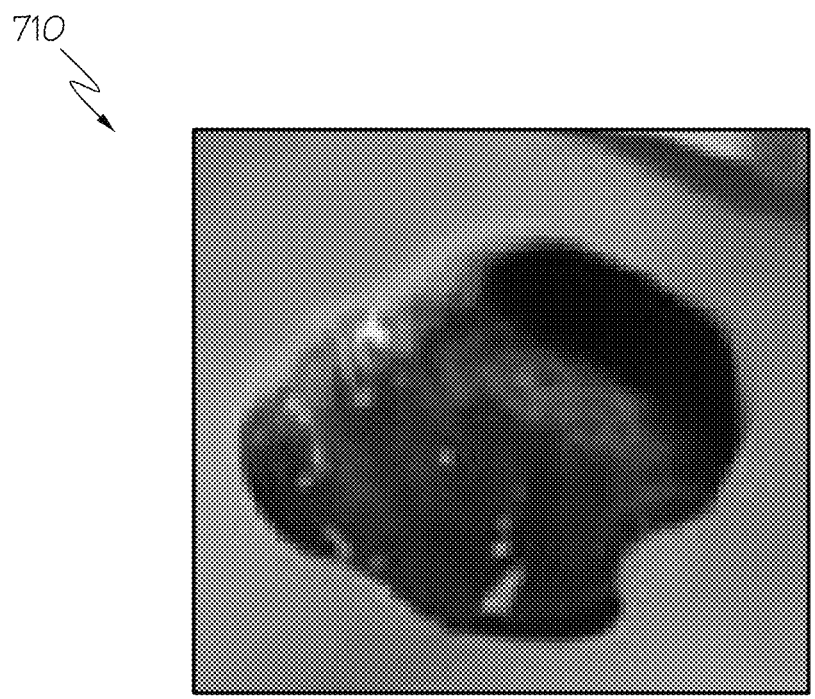
FIG. 7A depicts a greyscale image of a wound according to one or more embodiments shown or described herein.
Figure 7B:
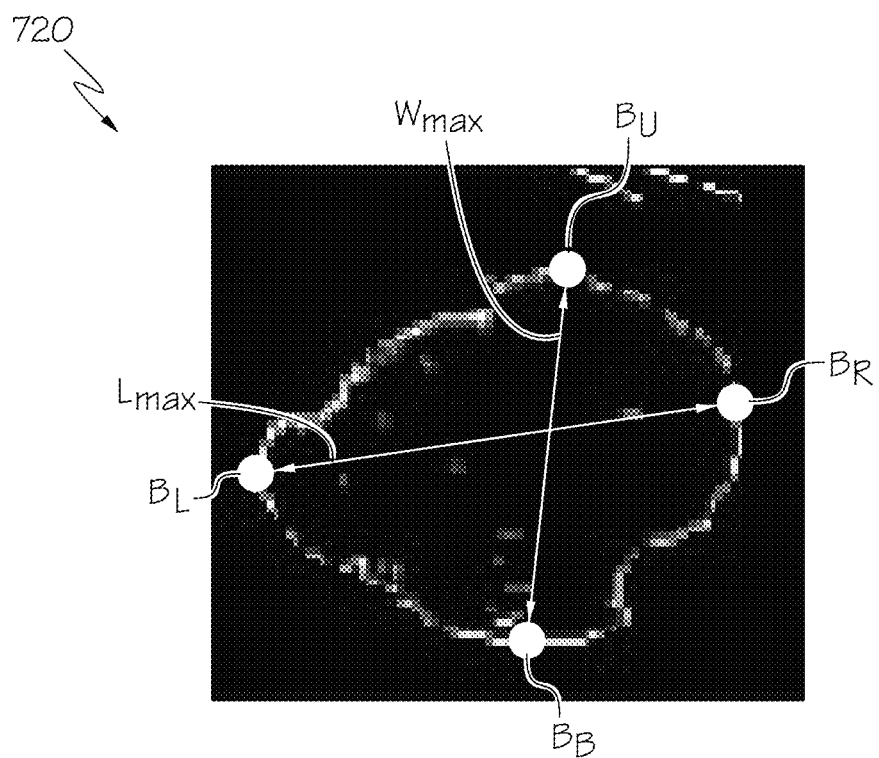
FIG. 7B depicts a pixel map of the greyscale image of the wound depicted in FIG. 7A according to one or more embodiments shown or described herein.

At step 440, the computing device 120 analyzes the greyscale image to determine the boundaries of the wound. That is, the computing device 120 analyzes the image and/or a region thereof for one or more pixel characteristics that may be indicative of a boundary, such as, for example, pixel color, pixel location relative to other pixels having the same or a similar color, pixel gradation, pixel intensity, and/or the like. In an illustrative example, the pixels may undergo binarization to aid in distinguishing wound pixels from non-wound pixels within the image. A threshold value may be used during binarization and may be determined from an intensity histogram of the image. In the image, wound border intensities may be blended with non-wound pixels, and non-wound pixels may be lighter than wound pixels, as illustrated, for example, by the black and white image 710 depicted in FIG. 7A. The wound edges are then detected by searching all rows and columns in the binarized image from a central portion moving outward until a non-wound (zero value) pixel is found. If additional non-wound pixels are found adjacent to the discovered non-wound pixel, an edge is assumed and the process repeats from the central portion in a different direction outward until the entire boundary has been discovered. The pixels are then drawn to a binary map of edge points, as illustrated in the map 720 depicted in FIG. 7B. It should be understood that the processes described herein for determining wound edges is merely illustrative, and any other image analysis may be automatically completed using any commercially available software now known or later developed that is particularly adapted for edge detection. One illustrative example of such a software program is MATLAB® (Mathworks, Natick Mass.). Another illustrative example of such a software program includes the programming functions that are available as part of OpenCV (Open Source Computer Vision Library).

Referring to FIGS. 1A-1B, 4, and 7A-7B, at step 440, the computing device 120 may compute the wound area (i.e., determine the wound size) based on the determined boundaries. For example, the computing device 120 may determine, from the map 720 a leftmost boundary location $B_L$, a rightmost boundary location $B_R$, a uppermost boundary location $B_U$, and a bottommost boundary location $B_B$. As used herein, the leftmost boundary location $B_L$ refers to a pixel within the boundary that is closest to the left side edge of the map 720, the rightmost boundary location $B_R$ refers to a pixel within the boundary that is closest to the right side edge of the map 720, the uppermost boundary location $B_U$ refers to a pixel within the boundary that is closest to the top edge of the map 720, and the bottommost boundary location $B_B$ refers to a pixel within the boundary that is closest to the bottom side edge of the map 720. The computing device 120 may then determine a maximum length $L_{max}$ that corresponds to the distance between the leftmost boundary location and the rightmost boundary location and a maximum width $W_{max}$ that corresponds to the distance between the topmost boundary location and the bottommost boundary location. The actual distances can be calculated by measuring the pixel distance on the map 720 and then imputing the actual distance between the points on the wound using Equation (1) described hereinabove. The maximum length and the maximum width may then by multiplied (i.e., $L_{max} \times W_{max}$) to obtain an approximate area of the wound. It should be understood that while this method does not provide an exact calculation of the area of the wound, a sufficient estimation is provided that can be used for the purposes of scoring the wound, as described herein. It should further be understood that other methods of calculating the wound size, including determining the actual wound size (instead of an estimation) may be used without departing from the scope of the present disclosure.

Referring again to FIGS. 1A-1B and 4, at step 450, the computing device 120 may score the wound based on the computed wound area to obtain a wound score. For example, the computing device 120 may determine the wound score based on a scoring chart 1105, as depicted in FIG. 11. That is, if the estimated area of the wound is about 9 square centimeters ($cm^2$), the wound may be assigned a score of 8, as the scoring chart 1105 indicates that a score of 8 is assigned to any wound having an area of about 8.1 $cm^2$ to about 12.0 $cm^2$. It should be understood that the scoring chart 1105 depicted in FIG. 11 is only one illustrative scoring chart, and other scores may be imputed to the wound size without departing from the scope of the present disclosure. The scoring chart 1105 may be a particular chart that is provided according to the wound scoring method, such as the PUSH and BWAT wound scoring methods described herein. In some embodiments, the scoring chart 1105 may be stored as a look-up table (LUT) in a storage location, such as, for example, the RAM 282, the ROM 284 (FIG. 2C) or in the server computing device 320 (FIG. 3). In addition, the wound score may be indexed according to wound area such that the computing device 120 can reference the determined wound area with a wound score from the LUT.

Referring to FIGS. 1A-1B, 3, and 4, the computing device 120 may transmit data containing the wound score at step 455. For example, the wound score, image data, greyscale image, and/or pixel map may be transmitted to an external device, such as the user computing device 310 and/or the server computing device 320. Such a transmission may be completed, for example, to store the data for later comparison, as described herein. In addition, the data may be transmitted, for example, to the user computing device 310 so that medical personnel not located with the subject may observe the wound, provide recommendations, provide prescriptions, provide a diagnosis, and/or the like via the user computing device 310.

At step 460, the computing device 120 determines whether additional imaging (i.e., monitoring) of the subject and/or a wound on the subject is necessary. Such a determination may generally be based on one or more inputs received from a user and/or may be based on the type of monitoring for which the device 100 is configured. For example, in some embodiments, a user may utilize the device 100 to image more than one wound on a subject, where each wound is individually imaged. That is, if a subject has a plurality of pressure wounds, the user of the device 100 may utilize the device 100 to image each one of the plurality of pressure wounds. If additional imaging is needed, the computing device 120 may direct the user to adjust the position of the device 100 at step 465. For example, the display 125 may display a user interface that provides instructions to the user to particularly position the device 100 such that the device 100 is aimed at another portion of the subject and/or aimed at a different wound. Accordingly, the user moves the device at step 470 and the process repeats at step 405.

If no additional imaging is needed or necessary, the process may end. It should be understood that, in some embodiments, the process described herein with respect to FIG. 4 ends for a particular imaging session. A user may subsequently image the wounds on a subject using the device 100 and the steps described with respect to FIG. 4 at any time thereafter. For example, medical personnel may direct the user to image the wounds on the subject according to the steps described herein with respect to FIG. 4 periodically, such as once a day, once a week, once a month, and/or the like.

In addition to determining a size of the wound, the computing device 120 may also (or alternatively) determine other characteristics of the wound, such as, for example, the type of tissue. For example, the wound may include tissue such as closed tissue, epithelial tissue, granulation tissue, slough, and necrotic tissue. One illustrative process that may be carried out by the device 100 in determining a tissue type of the wound based is depicted in the flow diagram of FIG. 8.

Figure 8:
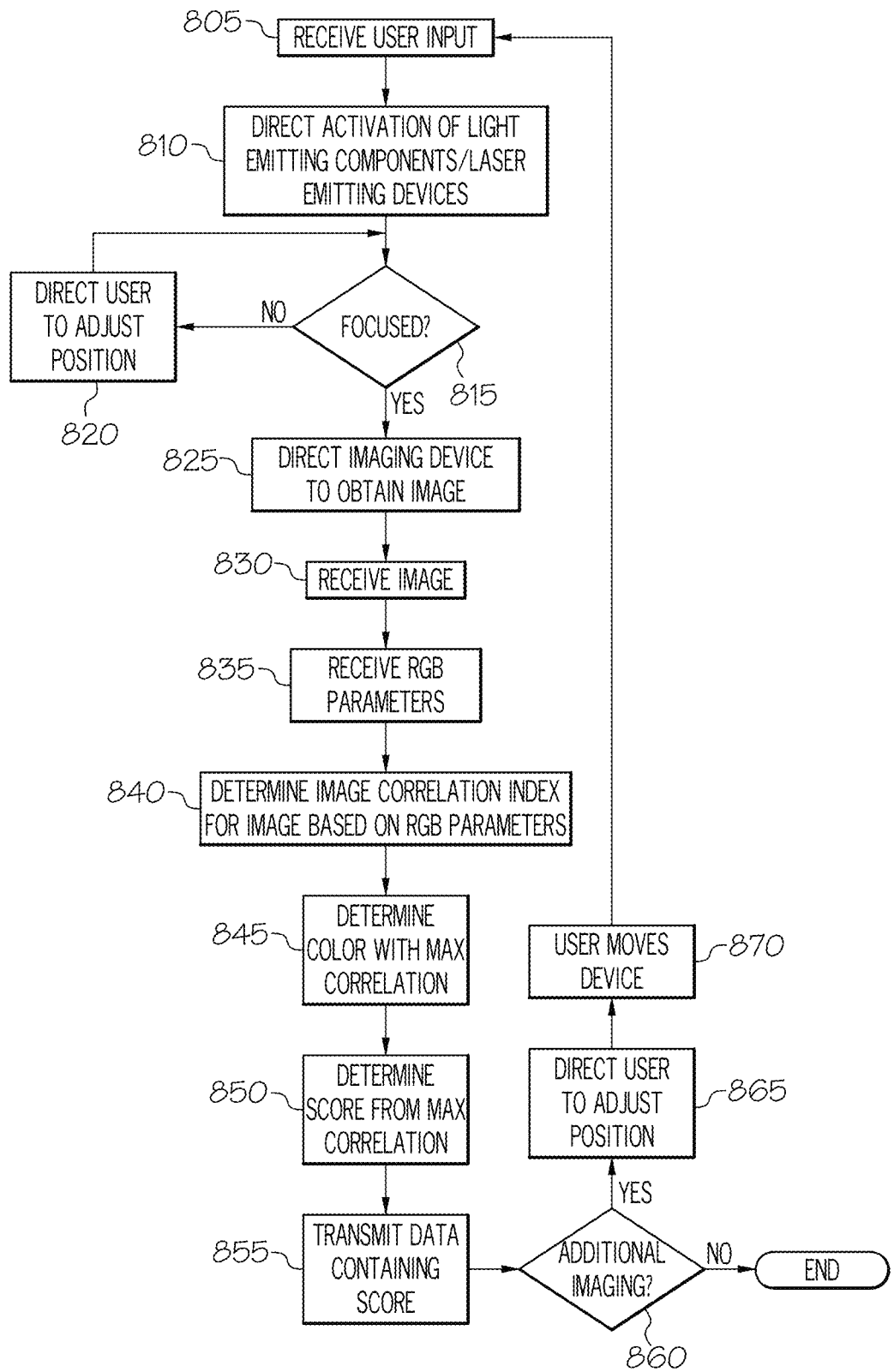
FIG. 8 depicts a flow diagram of an illustrative method of determining a tissue type according to one or more embodiments shown or described herein.

Referring to FIGS. 1A-1B and 8, at step 805, the computing device 120 may receive a user input to begin imaging. For example, the user may depress the trigger 135 to begin imaging. It should be understood that step 805 is optional. That is, in some embodiments, the computing device 120 may not receive a user input to begin imaging. For example, the computing device 120 may recognize when a wound is within the field of view of the imaging device 115 and begin imaging, or the computing device 120 may be in an "always on" state when powered on such that it is ready to complete the various processes described with respect to FIG. 8 without any user input.

In some embodiments, the computing device 120 may direct the one or more light emitting components 140 to emit the calibrated light to illuminate the target object for imaging and/or direct the one or more laser emitting devices 145 to project a laser towards the target object to ensure that the device 100 is appropriately positioned with respect to the target object at step 810. For example, the computing device 120 may transmit a signal to the imaging component 110 to cause the imaging component 110 to direct the one or more light emitting components 140 to emit light at a particular wavelength. In another example, the computing device 120 may transmit a signal to the imaging component 110 to cause the imaging component 110 to direct the one or more laser emitting devices 145 to project a laser. In some embodiments, the computing device 120 may transmit a signal to the imaging component 110 to cause the imaging component to first direct the one or more laser emitting devices 145 to project a laser, and then subsequently direct the one or more light emitting components 140 to project the calibrated light and correspondingly deactivate the laser emitted from the one or more laser emitting devices 145.

Accordingly, at step 815, a determination may be made as to whether the device 100 is appropriately positioned such that the image of the target object in the imaging component 110 is focused. As previously described herein with respect to FIGS. 4-5 and 6A-6C, the one or more laser emitting devices 145 may be utilized to ensure that the device 100 is positioned at a particular distance from the target object (e.g., the wound) to ensure that the target object is appropriately focused for imaging.

Referring again to FIGS. 1A-1B and 8, if the device 100 is not appropriately positioned, resulting in an unfocused image of the target object, the process may proceed to step 820 whereby the user is directed to adjust the positioning of the device 100. For example, the display 125 may display a user interface that provides instructions to the user to particularly position the device 100, such as by providing a diagram or the like indicating how the laser lines 610a, 610b, 610c described herein with respect to FIG. 6 are to be aligned by adjusting the location and/or positioning of the device 100 relative to the target object. The process may repeat at step 815 until the device 100 is appropriately positioned with respect to the target object.

If the device 100 is appropriately positioned to receive a focused image, the computing device 120 may direct the imaging device 115 to obtain the image at step 825. For example, the computing device 120 may direct the imaging device 115 by transmitting a signal to the imaging device 115 or transmitting a signal to the imaging component 110, which then directs the imaging device 115. It should be understood that step 825 is optional. That is, in some embodiments, the imaging device 115 may obtain images and/or transmit data without direction from the computing device 120. For example, the imaging device 115 may automatically obtain images and/or transmit data when powered on.

At step 830, the computing device 120 receives the image from the imaging device 115 via the imaging component 110. The image may be in the form of image data. Thus, the image may be transmitted as image data from the imaging device 115 to the computing device 120 via the imaging component 110. In addition, the computing device 120 receives or accesses RGB parameters at step 835. The RGB parameters may provide a basis for determining the color of the tissue, which, in turn, is used to determine the type of tissue. For example, the RGB parameters may be a look up table, a sample image, a color map, and/or the like containing color samples, computer recognizable code corresponding to color, and/or the like that can be accessed and used to compare each sample with the color of the wound in the image. In addition, the RGB parameters may represent colors that are imaged based on the wavelength of the light emitted from the one or more light emitting components 140 such that the RGB parameters accurately correspond to colors that are imaged. Illustrative colors that may be contained within the RGB parameters include, but are not limited to, black, brown, yellow, white, red, and pink, where each of the colors corresponds to a particular type of tissue. The RGB parameters may be received or accessed from a storage device, such as, for example, the RAM 282, the ROM 284 (FIG. 2C), storage located within the server computing device 320 (FIG. 3), and/or the like.

Still referring to FIGS. 1A-1B and 8, the computing device 120 may determine an image correlation index based on the RGB parameters at step 840. For example, a normalized correlation may be used as a similarity measurement between a color from the RGB parameters and a color obtained from one or more pixels in the image of the wound (i.e., the imaged color of the wound). Equation (2) below provides an example normalized correlation (NC) that may be used:

$$NC = \frac{\sum_{i=0}^{M-1}\sum_{j=0}^{M-1} W(i,j) W_R(i,j)}{\sum_{i=0}^{M-1}\sum_{j=0}^{M-1} [W(i,j)^2]} \quad (2)$$

where $W(i,j)$ is the color from the RGB parameters at a particular coordinate location i, j and $W_R(i,j)$ is the color of a pixel from the image obtained of the wound at a particular coordinate location i, j, where each image respectively has a size of M×M pixels.

Accordingly, Equation (2) may be used to compare the normalized correlation between the color of the one or more pixels from the obtained image and each of the colors from the RGB parameters. The color from the RGB parameters that results in the highest normalized correlation number (i.e., max correlation) may be selected as the determined color according to step 845.

Still referring to FIGS. 1A-1B and 8, at step 850, the computing device 120 may score the wound based on the max correlation, where the score represents a tissue type. For example, if the max correlation indicates that the tissue color is black, brown, or tan, the tissue may be determined to be necrotic. If the max correlation indicates that the tissue is yellow or white, the tissue may be determined to be slough. If the max correlation indicates that the tissue is pink or beefy red, the tissue may be determined to be granulation tissue. If the max correlation indicates that the tissue is a light pink color, the tissue may be determined to be epithelial tissue. If the max correlation indicates that the tissue is any other color (i.e., any normal skin color), the tissue may be determined to be closed or resurfaced tissue (i.e., a healed wound). The computing device 120 may then determine a wound score based on a scoring chart 1115, as depicted in FIG. 11. That is, if the max correlation indicates that the tissue is slough, the wound may be assigned a wound score of 3, as the scoring chart 1115 indicates that a score of 3 is assigned to slough. It should be understood that the scoring chart 1115 depicted in FIG. 11 is only one illustrative scoring chart, and other scores may be imputed to the tissue type without departing from the scope of the present disclosure. The scoring chart 1115 may be a particular chart that is provided according to the wound scoring method, such as the PUSH and BWAT wound scoring methods described herein. In some embodiments, the scoring chart 1115 may be stored as a LUT in a storage location, such as, for example, the RAM 282, the ROM 284 (FIG. 2C) or in the server computing device 320 (FIG. 3). In addition, the wound score may be indexed according to wound color (i.e., a computer-recognizable number or code referencing a particular color) such that the computing device 120 can reference the determined wound color with a wound score from the LUT.

Referring to FIGS. 1A-1B, 3, and 8, the computing device 120 may transmit data containing the wound score at step 855. For example, the wound score, image data, max correlation, tissue type, and/or the like may be transmitted to an external device, such as the user computing device 310 and/or the server computing device 320. Such a transmission may be completed, for example, to store the data for later comparison, as described herein. Such a transmission may also completed, for example, such that medical personnel not located with the subject may observe the wound, provide recommendations, provide prescriptions, provide a diagnosis, and/or the like.

At step 860, the computing device 120 determines whether additional imaging (i.e., monitoring) of the subject and/or a wound on the subject is necessary, as described in greater detail with respect to step 460 in FIG. 4. Still referring to FIGS. 1A-1B, 3, and 8, if additional imaging is needed, the computing device 120 may direct the user to adjust the position of the device 100 at step 865. Accordingly, the user moves the device at step 870 and the process repeats at step 805.

If no additional imaging is needed or necessary, the process may end. It should be understood that, in some embodiments, the process described herein with respect to FIG. 8 ends for a particular imaging session. A user may subsequently image the wounds on a subject using the device 100 and the steps described with respect to FIG. 8 at any time thereafter. For example, medical personnel may direct the user to image the wounds on the subject according to the steps described herein with respect to FIG. 8 periodically, such as once a day, once a week, once a month, and/or the like.

In addition to determining a size of the wound and/or a tissue type, the computing device 120 may also (or alternatively) determine other characteristics of the wound, such as, for example, an amount of exudate secreted by the wound. For example, the wound, depending on the state, may secrete an amount of exudate that can be used to determine whether the wound is healing or worsening. Exudate may be measured as described herein after measurement of the size of the wound as described with respect to FIG. 4 and after a bandage has been placed over the wound such that the bandage can collect the exudate that is secreted from the wound. One illustrative process that may be carried out by the device 100 in determining an amount of exudate secreted by the wound based is depicted in the flow diagram of FIG. 9.

Figure 9:
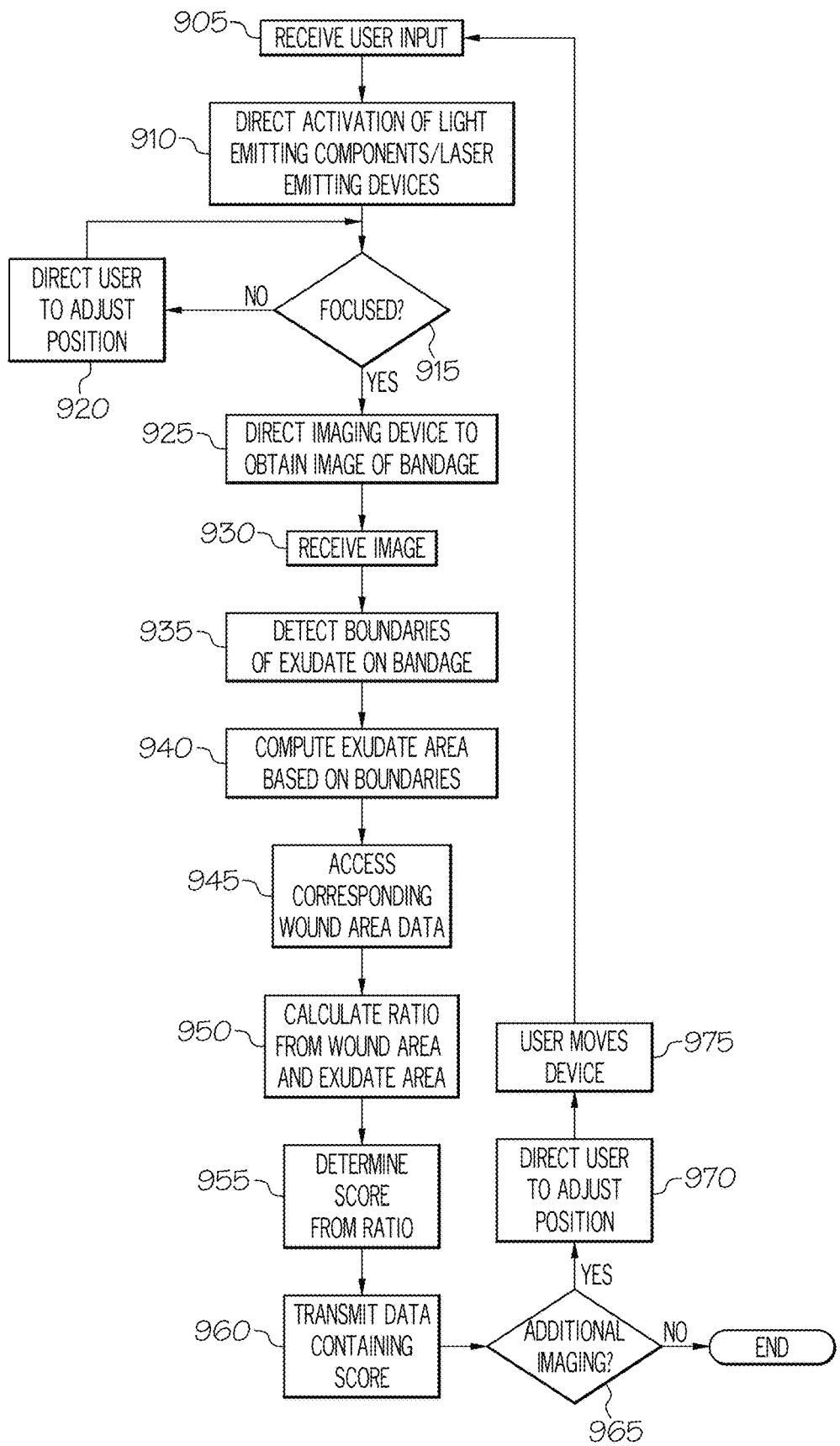
FIG. 9 depicts a flow diagram of an illustrative method of determining an amount of exudate according to one or more embodiments shown or described herein.

Referring to FIGS. 1A-1B and 9, at step 905, the computing device 120 may receive a user input to begin imaging. For example, the user may depress the trigger 135 to begin imaging. It should be understood that step 905 is optional. That is, in some embodiments, the computing device 120 may not receive a user input to begin imaging. For example, the computing device 120 may recognize when a wound is within the field of view of the imaging device 115 and begin imaging, or the computing device 120 may be in an "always on" state when powered on such that it is ready to complete the various processes described with respect to FIG. 9 without any user input.

In some embodiments, the computing device 120 may direct the one or more light emitting components 140 to emit the calibrated light to illuminate the target object for imaging and/or direct the one or more laser emitting devices 145 to project a laser towards the target object to ensure that the device 100 is appropriately positioned with respect to the target object at step 910. For example, the computing device 120 may transmit a signal to the imaging component 110 to cause the imaging component 110 to direct the one or more light emitting components 140 to emit light at a particular wavelength. In another example, the computing device 120 may transmit a signal to the imaging component 110 to cause the imaging component 110 to direct the one or more laser emitting devices 145 to project a laser. In some embodiments, the computing device 120 may transmit a signal to the imaging component 110 to cause the imaging component to first direct the one or more laser emitting devices 145 to project a laser, and then subsequently direct the one or more light emitting components 140 to project the calibrated light and correspondingly deactivate the laser emitted from the one or more laser emitting devices 145.

Accordingly, at step 915, a determination may be made as to whether the device 100 is appropriately positioned such that the image of the target object in the imaging component 110 is focused. As previously described herein with respect to FIGS. 4-5 and 6A-6C, the one or more laser emitting devices 145 may be utilized to ensure that the device 100 is positioned at a particular distance from the target object (e.g., the wound) to ensure that the target object is appropriately focused for imaging.

Referring again to FIGS. 1A-1B and 9, if the device 100 is not appropriately positioned, resulting in an unfocused image of the target object, the process may proceed to step 920 whereby the user is directed to adjust the positioning of the device 100. For example, the display 125 may display a user interface that provides instructions to the user to particularly position the device 100, such as by providing a diagram or the like indicating how the laser lines 610$a$, 610$b$, 610$c$ described herein with respect to FIG. 6 are to be aligned by adjusting the location and/or positioning of the device 100 relative to the target object. The process may repeat at step 915 until the device 100 is appropriately positioned with respect to the target object.

If the device 100 is appropriately positioned to receive a focused image, the computing device 120 may direct the imaging device 115 to obtain the image at step 925. For example, the computing device 120 may direct the imaging device 115 by transmitting a signal to the imaging device 115 or transmitting a signal to the imaging component 110, which then directs the imaging device 115. It should be understood that step 925 is optional. That is, in some embodiments, the imaging device 115 may obtain images and/or transmit data without direction from the computing device 120. For example, the imaging device 115 may automatically obtain images and/or transmit data when powered on.

At step 930, the computing device 120 receives the image from the imaging device 115 via the imaging component 110. The image may be in the form of image data. Thus, the image may be transmitted as image data from the imaging device 115 to the computing device 120 via the imaging component 110. In addition, the computing device 120 detects the boundaries of the exudate on the bandage at step 935. Such an edge detection is similar to the edge detection described herein with respect to FIGS. 4 and 7A-7B. As part of detecting the boundaries of the exudate, the computing device 120 may further determine that a bandage is covering the wound, which may be completed by analyzing the colors of the image to determine whether the colors correspond to wound colors or bandage colors, similar to the color analysis described hereinabove with respect to FIG. 8. Such an analysis may occur, for example, prior to conversion of the RGB image to a greyscale image.

Still referring to FIGS. 1A-1B and 9, the computing device 120 may calculate the area of the exudate at step 940. Such an area calculation may be completed in a manner similar to that described herein with respect to FIGS. 4 and 7A-7B.

In order for the exudate to be scored, the wound size may first be determined, as described herein with respect to FIG. 4. Once the wound size has been determined and the data relating to the size of the wound has been recorded, it may be accessed by the computing device 120 for the purposes of scoring the exudate area. Accordingly, while still referring to FIGS. 1A-1B and 9, data relating to the previous measurement of the wound size may be accessed by the computing device 120 at step 945. For example, the computing device 120 may access the RAM 282, the ROM 284 (FIG. 2C), storage located within the server computing device 320 (FIG. 3), and/or the like to obtain stored data relating to the wound size. Still referring to FIGS. 1A-1B and 9, at step 950, a ratio ($A_{ratio}$) of the exudate area ($A_{wet}$) to the wound area ($A_{would}$) may be calculated according to Equation (3):

$$A_{ratio} = \frac{A_{wet}}{A_{wound}} \quad (3)$$

The resulting ratio may be any number between 0 and 1. For example, if the exudate area is 6 cm² and the wound area is 9 cm², then the ratio would be 6/9 or 0.67.

At step 955, the computing device 120 may determine a score based on the calculated ratio, where the score represents an exudate amount. For example, if the ratio is zero, the amount of exudate is also zero. If the ratio is less than 0.25, the computing device 120 may determine that a light amount of exudate exists. If the ratio is greater than or equal to 0.25 and less than or equal to 0.75, the computing device 120 may determine that a moderate amount of exudate exists. If the ratio is greater than 0.75, the computing device 120 may determine that a heavy amount of exudate exists. The computing device 120 may then determine a wound score based on a scoring chart 1110, as depicted in FIG. 11. That is, if the ratio indicates that the amount of exudate is moderate, the wound may be assigned a wound score of 2, as the scoring chart 1110 indicates that a score of 2 is assigned to a moderate amount of exudate. It should be understood that the scoring chart 1110 depicted in FIG. 11 is only one illustrative scoring chart, and other scores may be imputed to the amount of exudate without departing from the scope of the present disclosure. The scoring chart 1110 may be a particular chart that is provided according to the wound scoring method, such as the PUSH and BWAT wound scoring methods described herein. In some embodiments, the scoring chart 1110 may be stored as a look-up table (LUT) in a storage location, such as, for example, the RAM 282, the ROM 284 (FIG. 2C) or in the server computing device 320 (FIG. 3). In addition, the wound score may be indexed according to exudate amount such that the computing device 120 can reference the determined exudate area on the bandage with a wound score from the LUT.

Referring to FIGS. 1A-1B, 3, and 9, the computing device 120 may transmit data containing the wound score at step 960. For example, the wound score, image data, measurements, ratio, determined amount of exudate, and/or the like may be transmitted to an external device, such as the user computing device 310 and/or the server computing device 320. Such a transmission may be completed, for example, to store the data for later comparison, as described herein. Such a transmission may also completed, for example, such that medical personnel not located with the subject may observe the wound, provide recommendations, provide prescriptions, provide a diagnosis, and/or the like.

At step 965, the computing device 120 determines whether additional imaging (i.e., monitoring) of the subject and/or a wound on the subject is necessary, as described in greater detail with respect to step 460 in FIG. 4. Still referring to FIGS. 1A-1B, 3, and 9, if additional imaging is needed, the computing device may direct the user to adjust the position of the device 100 at step 970. Accordingly, the user moves the device at step 975 and the process repeats at step 905.

If no additional imaging is needed or necessary, the process may end. It should be understood that, in some embodiments, the process described herein with respect to FIG. 9 ends for a particular imaging session. A user may subsequently image the wounds on a subject using the device 100 and the steps described with respect to FIG. 9 at any time thereafter. For example, medical personnel may direct the user to image the wounds on the subject according to the steps described herein with respect to FIG. 9 periodically, such as once a day, once a week, once a month, and/or the like.

In some embodiments, the wound may be tracked over a period of time such that a determination can be made as to whether the wound is healing, remaining the same, or worsening. As such, historical data relating to previous imaging of the wound may be accessed such that a comparison can be made. One illustrative process that may be carried out by the device 100 in determining one or more updated characteristics of the wound is depicted in the flow diagram of FIG. 10.

Figure 10:
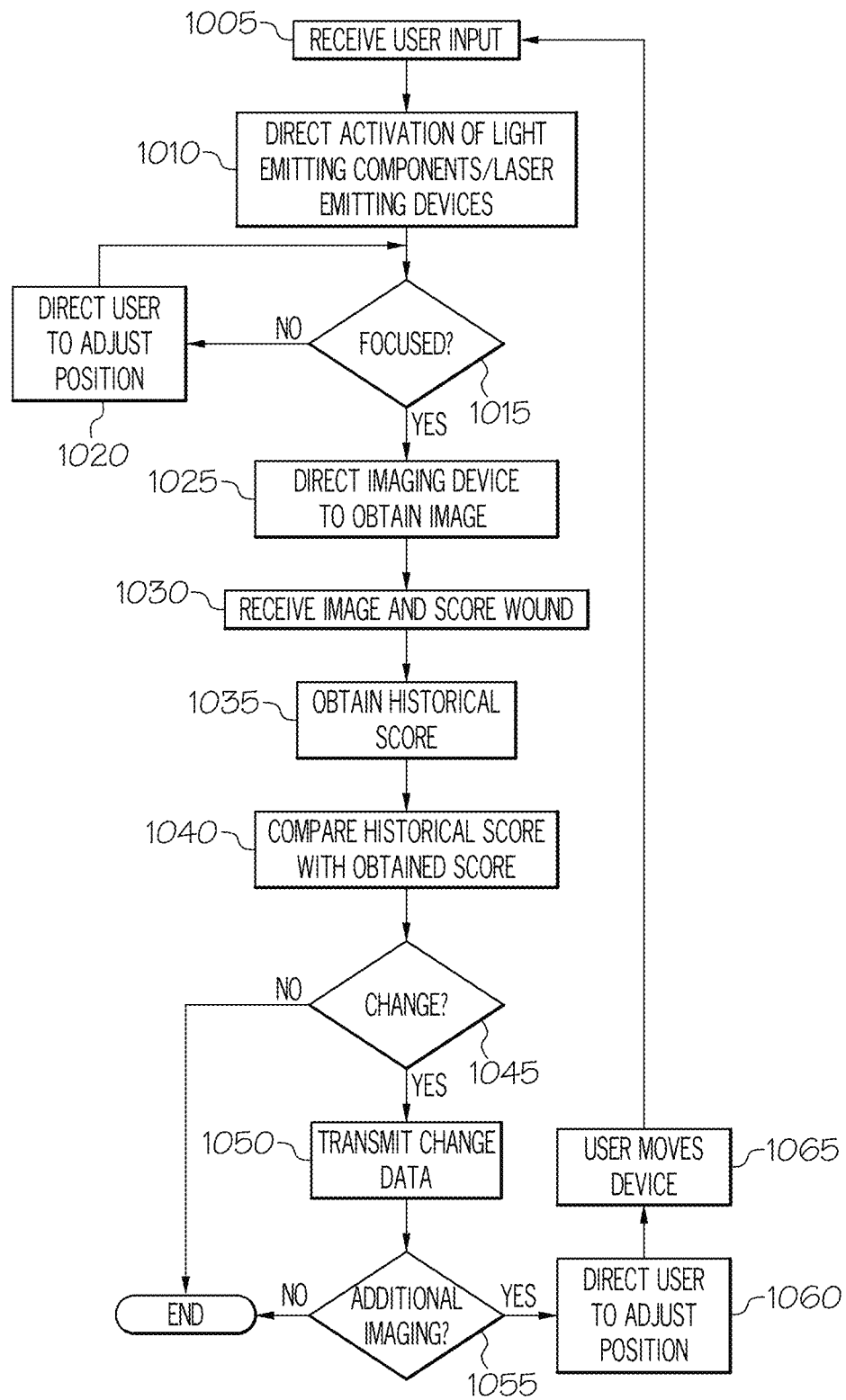
FIG. 10 depicts a flow diagram of an illustrative method of determining a change in wound features according to one or more embodiments shown or described herein.

Referring to FIGS. 1A-1B and 10, at step 1005, the computing device 120 may receive a user input to begin imaging. For example, the user may depress the trigger 135 to begin imaging. It should be understood that step 1005 is optional. That is, in some embodiments, the computing device 120 may not receive a user input to begin imaging. For example, the computing device 120 may recognize when a wound is within the field of view of the imaging device 115 and begin imaging, or the computing device 120 may be in an "always on" state when powered on such that it is ready to complete the various processes described with respect to FIG. 10 without any user input.

In some embodiments, the computing device 120 may direct the one or more light emitting components 140 to emit the calibrated light to illuminate the target object for imaging and/or direct the one or more laser emitting devices 145 to project a laser towards the target object to ensure that the device 100 is appropriately positioned with respect to the target object at step 1010. For example, the computing device 120 may transmit a signal to the imaging component 110 to cause the imaging component 110 to direct the one or more light emitting components 140 to emit light at a particular wavelength. In another example, the computing device 120 may transmit a signal to the imaging component 110 to cause the imaging component 110 to direct the one or more laser emitting devices 145 to project a laser. In some embodiments, the computing device 120 may transmit a signal to the imaging component 110 to cause the imaging component to first direct the one or more laser emitting devices 145 to project a laser, and then subsequently direct the one or more light emitting components 140 to project the calibrated light and correspondingly deactivate the laser emitted from the one or more laser emitting devices 145.

Accordingly, at step 1015, a determination may be made as to whether the device 100 is appropriately positioned such that the image of the target object in the imaging component 110 is focused. As previously described herein with respect to FIGS. 4-5 and 6A-6C, the one or more laser emitting devices 145 may be utilized to ensure that the device 100 is positioned at a particular distance from the target object (e.g., the wound) to ensure that the target object is appropriately focused for imaging.

Referring again to FIGS. 1A-1B and 10, if the device 100 is not appropriately positioned, resulting in an unfocused image of the target object, the process may proceed to step 1020 whereby the user is directed to adjust the positioning of the device 100. For example, the display 125 may display a user interface that provides instructions to the user to particularly position the device 100, such as by providing a diagram or the like indicating how the laser lines 610*a*, 610*b*, 610*c* described herein with respect to FIG. 6 are to be aligned by adjusting the location and/or positioning of the device 100 relative to the target object. The process may repeat at step 1015 until the device 100 is appropriately positioned with respect to the target object.

If the device 100 is appropriately positioned to receive a focused image, the computing device 120 may direct the imaging device 115 to obtain the image at step 1025. For example, the computing device 120 may direct the imaging device 115 by transmitting a signal to the imaging device 115 or transmitting a signal to the imaging component 110, which then directs the imaging device 115. It should be understood that step 1025 is optional. That is, in some embodiments, the imaging device 115 may obtain images and/or transmit data without direction from the computing device 120. For example, the imaging device 115 may automatically obtain images and/or transmit data when powered on.

At step 1030, the computing device 120 receives the image from the imaging device 115 via the imaging component 110 and scores the wound. The image may be in the form of image data. Thus, the image may be transmitted as image data from the imaging device 115 to the computing device 120 via the imaging component 110. The wound may be scored using any scoring method, including the various scoring methods described herein with respect to FIGS. 4, 8, and 9 to obtain one or more wound scores.

In addition, the computing device 120 receives one or more historical scores at step 1035. For example, the computing device 120 may access the RAM 282, the ROM 284 (FIG. 2C), storage located within the server computing device 320 (FIG. 3), and/or the like to obtain one or more historical stored scores relating to the various wound characteristics. In addition to historical scores, the computing device 120 may also obtain other related data regarding the wound size, the tissue type, and/or the amount of exudate. The other related data may be the actual data that was determined/calculated, images of the wound, and/or the like. In addition, to ensure that the correct historical data is obtained, the wound indicator for the historical score and related data may be matched with the wound indicator of the newly obtained image and score.

Still referring to FIGS. 1A-1B and 10, the computing device 120 may compare the historical scores with the newly determined wound score for one or more of the wound characteristics at step 1040 and determine at step 1045 whether a change occurred based on the comparison. For example, if the historical score for a particular wound included a size score of 8, an exudate score of 2, and a tissue type of 2 for a total score of 12, a change may be determined if the newly obtained wound score according to step 1030 is different. If no change is present (i.e., the newly obtained wound scores match the corresponding historical scores), the process may end. If a change is present (i.e., the newly obtained wound scores are higher or lower than the corresponding historical scores), the computing device 120 may transmit the change data at step 1050. For example, the newly obtained wound score, image data, measurements, ratio, determined amount of exudate, and/or the like may be transmitted to an external device, such as the user computing device 310 and/or the server computing device 320 (FIG. 3). Such a transmission may be completed, for example, to store the data for later comparison, as described herein. Such a transmission may also completed, for example, such that medical personnel not located with the subject may observe the wound, provide recommendations, provide prescriptions, provide a diagnosis, and/or the like.

Still referring to FIGS. 1A-1B and 10, at step 1055, the computing device 120 determines whether additional imaging (i.e., monitoring) of the subject and/or a wound on the subject is necessary, as described in greater detail with respect to step 460 in FIG. 4. Still referring to FIGS. 1A-1B, and 10, if additional imaging is needed, the computing device 120 may direct the user to adjust the position of the device 100 at step 1060. Accordingly, the user moves the device at step 1065 and the process repeats at step 1005.

If no additional imaging is needed or necessary, the process may end. It should be understood that, in some embodiments, the process described herein with respect to FIG. 10 ends for a particular imaging session. A user may subsequently image the wounds on a subject using the device 100 and the steps described with respect to FIG. 10 at any time thereafter. For example, medical personnel may direct the user to image the wounds on the subject according to the steps described herein with respect to FIG. 10 periodically, such as once a day, once a week, once a month, and/or the like.

Referring again to FIGS. 1A-1B and 6A, a user that uses the device 100 to image a wound generally positions the device 100 such that the imaging component 110 is facing the wound. The user may follow one or more instructions provided via a user interface on the display 125 to appropriately aim the device 100 at the wound. In addition, the user may adjust the positioning and/or location of the device 100 relative to the wound such that the projected laser lines intersect at the location of the wound, as described herein. The user may also view a live image of the wound on the display 125 to ensure that an image of the wound will include the entire wound. The user may optionally select, via the user interface, one or more characteristics to be determined as a result of the imaging process, including, but not limited to, the wound size, an amount of exudate, and a type of tissue. Optionally, the user may depress the trigger 135 to begin imaging.

If the characteristics to be determined include the amount of exudate and one or more of the wound size and tissue type, the user may remove or place a bandage between successive imaging sessions. For example, if exudate and tissue type are measured and a bandage is already present over the wound, the user may first use the device 100 to image the bandage, determine the characteristics of the exudate, and score the exudate. Subsequently, the user may then remove the bandage from the wound and utilize the device 100 to image the wound, determine the characteristics of the tissue, and score the tissue.

Optionally, the user may select a user interface option to compare the newly-obtained wound characteristics with historical characteristics, which may cause the device 100 to function as described herein with respect to FIG. 10. Referring to FIGS. 1A-1B, the user may optionally select an option in the user interface to transmit data to one or more external sources, such as an external server or to a medical provider's computer. Alternatively, the data may be automatically transmitted, as described in greater detail herein.

The user may optionally repeat any one or more of the steps above for each wound to be imaged and/or scored. In addition, the user may optionally repeat any one or more of the steps above periodically such that the status of the wound can be monitored and a determination can be made as to whether the wound is healing, remaining the same, or worsening.

It should now be understood that the device according to the present disclosure accurately determines one or more characteristics of a wound on a subject and scores the wound based on the determined characteristics using an imaging component communicatively coupled to a computing device. In addition, the device according to the present disclosure is compact, hand held, and is easily used by a layman because several or all of the processes necessary to determine the characteristics of the wound and/or score the wound can be completed automatically without user inputs. As a result, the device can be used by any individual, including non-medical personnel. In addition, the device allows for monitoring of wounds outside of a medical facility, but contains functionality that allows medical personnel to remotely monitor the wound and take appropriate action.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A monitoring device comprising:
an imaging component comprising:
a light emitting component that emits light at a calibrated wavelength,
a laser emitting device, and
an imaging device; and
a computing device communicatively coupled to the imaging component, wherein the computing device:
directs the light emitting component to emit the light at the calibrated wavelength,
directs the imaging component to cause the laser emitting device to emit a laser projection toward a wound,
receives, from the imaging component, image data captured by the imaging device,
determines, from the image data, an amount of exudate by determining that a bandage is covering the wound, detecting a plurality of exudate boundaries present on the bandage, computing an exudate area from the plurality of exudate boundaries, accessing data relating to a baseline wound area, calculating a ratio of the baseline wound area to the exudate area, and determining the amount of exudate from the ratio, and
scores the wound based on the amount of exudate to obtain a wound score.

2. The monitoring device of claim 1, wherein the monitoring device is a handheld monitoring device.

3. The monitoring device of claim 1, wherein the computing device is physically detachable from the imaging component while maintaining communicative coupling with the imaging component.

4. The monitoring device of claim 1, further comprising a user interface that provides information to a user and receives one or more inputs from the user.

5. The monitoring device of claim 1, wherein the imaging device comprises an image sensor array that includes a photodiode control device that controls operation of a photodiode of the image sensor array, a shutter control device that controls operation of a shutter component of the image sensor array, and an opaque shielded storage device that records light incident on one or more pixels of the image sensor array.

6. The monitoring device of claim 1, wherein the computing device determines a size of the wound by converting the image data into a greyscale image, detecting a plurality of boundaries of the wound from the greyscale image, and computing a wound area from the plurality of boundaries.

7. The monitoring device of claim 1, wherein the computing device determines a type of tissue by obtaining red, green, blue (RGB) parameters from the image data, determining an image correlation index based on the RGB parameters, determining a color from the image correlation index, and utilizing the color to determine the type of tissue.

8. The monitoring device of claim 1, wherein the computing device further determines a change in one or more of a size of the wound, a type of tissue, and the amount of exudate by accessing a historical score and comparing the historical score with the wound score.

9. A monitoring device comprising:
an imaging component comprising:
a light emitting component that emits light at a calibrated wavelength,
a laser emitting device, and
an imaging device; and
a computing device communicatively coupled to the imaging component, the computing device comprising a processing device and a non-transitory, processor-readable storage medium, the non-transitory, processor-readable storage medium comprising one or more processor readable and executable instructions that, when executed, cause the processing device to:
direct the light emitting component to emit the light at the calibrated wavelength,
direct the imaging component to cause the laser emitting device to emit a laser projection toward a wound,
receive, from the imaging component, image data captured by the imaging device,
determine, from the image data, an amount of exudate by determining that a bandage is covering the wound, detecting a plurality of exudate boundaries present on the bandage, computing an exudate area from the plurality of exudate boundaries, accessing data relating to a baseline wound area, calculating a ratio of the baseline wound area to the exudate area, and determining the amount of exudate from the ratio, and
score the wound based on the amount of exudate to obtain a wound score.

10. The monitoring device of claim 9, wherein the non-transitory, processor-readable storage medium further comprises one or more processor readable and executable instructions that, when executed, cause the processing device to:
direct a user to position the imaging component such that the imaging component faces the wound without contacting the wound.

11. The monitoring device of claim 10, wherein the non-transitory, processor-readable storage medium further comprises one or more processor readable and executable instructions that, when executed, cause the processing device to:
receive, from the imaging component, an image of the laser projection on the wound;
determine, from the image, that the laser projection is not focused on the wound; and
direct the user to reposition the imaging component to adjust a focus of the laser projection.

12. The monitoring device of claim 9, wherein the non-transitory, processor-readable storage medium further comprises one or more processor readable and executable instructions that, when executed, cause the processing device to:
    convert the image data into a greyscale image;
    detect a plurality of boundaries of the wound from the greyscale image; and
    compute a wound area from the plurality of boundaries.

13. The monitoring device of claim 9, wherein the non-transitory, processor-readable storage medium further comprises one or more processor readable and executable instructions that, when executed, cause the processing device to:
    obtain red, green, blue (RGB) parameters from the image data;
    determine an image correlation index based on the RGB parameters;
    determine a color from the image correlation index; and
    utilize the color to determine a type of tissue.

14. The monitoring device of claim 9, wherein the non-transitory, processor-readable storage medium further comprises one or more processor readable and executable instructions that, when executed, cause the processing device to:
    access a historical score; and
    compare the historical score with the wound score to determine a change in one or more of a size of the wound, a type of tissue, and the amount of exudate.

15. The monitoring device of claim 9, wherein the one or more processor readable and executable instructions that, when executed, cause the processing device to score the wound further cause the processing device to:
    calculate the wound score via a wound assessment tool.

16. The monitoring device of claim 9, wherein the non-transitory, processor-readable storage medium further comprises one or more processor readable and executable instructions that, when executed, cause the processing device to:
    transmit the wound score to an external computing device.

17. A system comprising:
    a monitoring device comprising an imaging component having one or more light emitting components, one or more laser emitting devices, and an imaging device, wherein the monitoring device:
    directs placement of the monitoring device at a location adjacent to a wound without contacting the wound,
    emits, via a light emitting component, light at a calibrated wavelength,
    emits, via a laser emitting device, a laser projection toward the wound,
    captures, via the imaging device, image data corresponding to the wound,
    determines, from the image data, an amount of exudate by determining that a bandage is covering the wound, detecting a plurality of exudate boundaries present on the bandage, computing an exudate area from the plurality of exudate boundaries, accessing data relating to a baseline wound area, calculating a ratio of the baseline wound area to the exudate area, and determining the amount of exudate from the ratio, and
    assigns a score to the wound based on the amount of exudate; and
    an external computing device communicatively coupled to the monitoring device, wherein the external computing device receives the score and provides the score to one or more users.

18. The system of claim 17, wherein the external computing device comprises a storage device that stores the score for future access.

* * * * *